United States Patent [19]

Zellner, deceased

[11] 4,012,389
[45] Mar. 15, 1977

[54] 2- OR 3-PHENYL 1,4-DISUBSTITUTED PHENYL PIPERAZINES

[75] Inventor: Hugo Zellner, deceased, late of Linz-Ebelsberg, Austria, by Gertroud Zellner, administratrix

[73] Assignee: Donau-Pharmazie Gesellschaft m.b.H., Linz, Austria

[22] Filed: Oct. 31, 1975

[21] Appl. No.: 627,690

Related U.S. Application Data

[60] Division of Ser. No. 333,497, Feb. 20, 1973, Pat. No. 3,935,214, which is a continuation-in-part of Ser. No. 848,395, July 23, 1969, abandoned.

[30] Foreign Application Priority Data

July 26, 1968 Austria .................. 7306/68

[52] U.S. Cl. .............. 260/268 R; 260/268 MK; 260/268 H; 260/246 B; 260/247.2; 260/247.5 D; 424/250
[51] Int. Cl.² ............. C07D 241/00; C07D 401/06
[58] Field of Search .............................. 260/268 R

[56] References Cited
UNITED STATES PATENTS 3,935,214  1/1976  Zellner .................. 260/268 MK

*Primary Examiner*—Donald G. Daus
*Assistant Examiner*—Jose Tovar
*Attorney, Agent, or Firm*—Erich M. H. Radde

[57] ABSTRACT

Novel 1,4-substituted phenyl piperazine compounds have a pronounced effect upon blood coagulation and are useful in the treatment of thrombotic diseases, especially of the arterial system. They are particularly used to inhibit thrombosis of the coronary or cerebral arteries. Examples of such compounds are 1-phenyl (lower) alkyl-2-phenyl-4-di-(lower)alkylamino (lower-)alkyl piperazines, 1-phenyl (lower)alkyl-3-phenyl-4-di-(lower)alkylamino (lower)alkyl piperazines and their pharmaceutically acceptable acid addition salts. The phenyl ring in 1-position may be substituted by halogen, trifluoro (lower)alkyl, lower alkoxy, or phenyl lower alkoxy; the di-(lower)alkylamino (lower)alkyl group in 4-position may be replaced by piperidino (lower)akyl, morpholino (lower)alkyl, pyrrolidino (lower)alkyl, piperazino (lower)alkyl, or the like mononuclear nitrogen-containing heterocyclically substituted (lower)alkyl.

14 Claims, No Drawings

2- OR 3-PHENYL 1,4-DISUBSTITUTED PHENYL PIPERAZINES

CROSS-REFERENCE TO RELATED APPLICATION

The present application is a division of copending Application Ser. No. 333,497, filed Feb. 20, 1973, now U.S. Pat. No. 3,935,214; issued Jan. 27, 1976, and entitled 2- OR 3-KETO-C-PHENYL-1,4-DISUBSTITUTED PIPERAZINES, said application Ser. No. 333,497 in turn being a continuation-in-part application of copending Application Ser. No. 848,395, filed July 23, 1969, and entitled 1,4-DISUBSTITUTED PHENYL PIPERAZINE COMPOUNDS, COMPOSITIONS CONTAINING SAME, AND PROCESS OF MAKING AND USING SAME, now abandoned.

BACKGROUND OF THE INVENTION

1. Field of the Invention

The present invention relates to new and valuable phenyl piperazine compounds and more particularly to 1,4-substituted phenyl piperazine compounds of noteworthy therapeutic utility and to a process of making and using same.

2. Description of the Prior Art

ARCHER in U.S. Pat. No. 3,062,821 discloses 1,4-disubstituted-2-piperazinones of Formula I

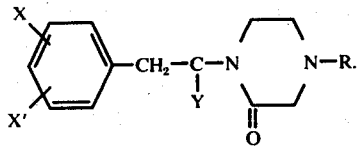

In said formula
R represents lower alkyl;
X and X' represent hydrogen, lower alkoxy, or hydroxyl; and
Y hydrogen or lower alkyl.
Said 1-[2-(phenyl lower alkyl)]-4-lower alkyl-2-piperazinone compounds are useful intermediates in the preparation of compounds of Formula II

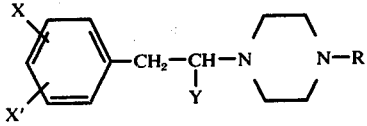

in which R, X, X', and Y represent the same substituents as given hereinabove. These 1-[2-(phenyl lower alkyl)]-4-lower alkyl piperazine compounds are useful hypotensive agents.

DE BENNEVILLE in U.S. Pat. No. 3,390,139 discloses N-vinyl-2-piperazinones of Formula III

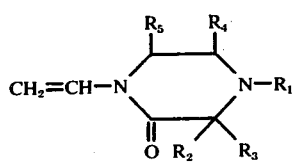

in which $R_1$ is hydrogen, alkyl, cycloalkyl, aralkyl, alkyl substituted aralkyl, diaminoalkyl, or furfuryl;
$R_2$ is hydrogen or methyl;
$R_3$ is hydrogen, alkyl, cycloalkyl, phenyl, naphthyl, alkyl, chloro, or alkoxy substituted phenyl or naphthyl, aralkyl, alkyl substituted aralkyl, or 2-furyl;
$R_4$ is hydrogen or alkyl; and
$R_5$ is hydrogen or alkyl.

These compounds are polymerizable or copolymerizable compounds, the resulting polymers or copolymers are useful for many purposes. Higher members of the monomeric N-vinyl-2-piperazinones of Formula III show fungistatic and bacteriostatic activity and are useful for other purposes.

DE BENNEVILLE in U.S. Pat. No. 2,653,153 describes 4-N-substituted-2-ketopiperazines of Formula IV

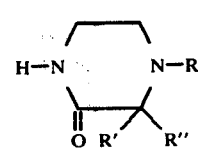

in which
R is alkyl, tertiary aminoalkyl, or aralkyl; and
R' and R" are hydrogen or lower alkyl. These 4-N-substituted-2-ketopiperazines are valuable activators and synergists for insecticidal agents.

None of these compounds has found any noteworthy application in veterinary and human therapy.

SUMMARY OF THE INVENTION

It is one object of the present invention to provide valuable 1,4-substituted phenyl piperazine compounds which have a surprising and pronounced effect upon blood coagulation and are useful, for instance, in the treatment of thrombotic diseases, especially those of the arterial system.

Another object of the present invention is to provide a simple and effective process of producing such valuable novel 1,4-substituted phenyl piperazine compounds.

A further object of the present invention is to provide pharmaceutical compositions containing, as active pharmaceutical agent, said novel 1,4-substituted phenyl piperazine compounds Still another object of the present invention is to provide a method of therapeutically affecting blood coagulation by administering the novel 1,4-substituted phenyl piperazine compounds.

Other objects of the present invention and advantageous features thereof will become apparent as the description proceeds.

In principle, the new 1,4-substituted phenyl piperazine compounds according to the present invention correspond to the following formula V

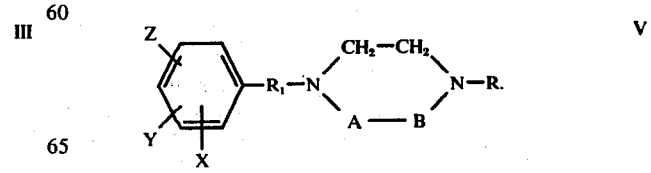

In said formula

X, Y, and Z are the same or different substituents and may be either hydrogen, halogen, trifluoro lower alkyl, preferably trifluoro methyl, hydroxyl, lower alkoxy, preferably methoxy or ethoxy, or phenyl substituted lower alkoxy, such as benzyloxy;

R is di-(lower)alkylamino (lower)alkyl, and preferably dimethylamino ethyl, diethylamino ethyl, dipropylamino ethyl, dimethylamino propyl, diethylamino propyl, di-n-propylamino propyl, or lower alkyl substituted by one or two saturated monocyclic heterocyclic rings such as piperidino, pyrrolidino, piperazino, N-lower alkyl piperazino, 3-ketopiperazino, morpholino, or the like, preferably piperidino ethyl, morpholino ethyl, or dimorpholino propyl;

$R_1$ is lower alkyl with 1 to 3 carbon atoms; and

is the group

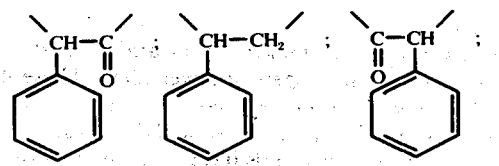

The term "lower alkyl" in said substituents indicates alkyl with 1 to 5 carbon atoms. Thus the substituent in $N_1$-position of the piperazine ring may be benzyl, phenyl ethyl, or phenyl propyl, or substituted benzyl, phenyl ethyl, phenyl propyl. Preferred substituents in the $N_1$-aralkyl group are One halogen atom in 2-; 3-; or 4-position.

Two halogen atoms in 2,3-; 2,4-; 2,5-; or 3,4- position and, if desired, also in 2,6-position.

Such halogen substituted compounds may also carry hydroxyl or lower alkoxy, preferably methoxy groups.

One lower alkoxy group, preferably one methoxy or ethoxy group in 4-position.

Three lower alkoxy groups, preferably in 3,4,5-position.

One phenyl lower alkoxy group, preferably the benzyloxy group in 2- or 4-position.

Two phenyl lower alkoxy groups, preferably the benzyloxy groups in 3,4-position.

Two hydroxyl groups, preferably in 2,3, and/or 4-position.

One trifluoro lower alkyl group, preferably the trifluoromethyl group in 3-position. addition The phenyl radical in position 2 or 3 of the piperazine ring is always unsubstituted.

The basic lower alkylamino group in $N_4$-position is preferably a group of the Formula VI

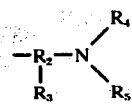

VI in which $R_2$ is lower alkyl;

$R_3$ is hydrogen or a saturated five- or six-membered heterocyclic ring, preferably the morpholino ring attached by its heterocyclic nitrogen atom to the lower alkyl $R_2$; and $R_4$ and $R_5$ are lower alkyl or, together with the nitrogen atom to which they are attached, form a saturated five- or six-membered heterocyclic ring, such as the pyrrolidino, piperidino, piperazino, or morpholino ring. The piperazino ring may be substituted at its other nitrogen atom by lower alkyl or by hydroxy lower alkyl to represent the $N_4$-lower alkyl or $N_4$-hydroxy lower alkyl piperazino ring or it may be substituted by a keto group to represent the 3-keto piperazino ring.

It is evident that the compounds according to the present invention represent two groups of compounds, namely a. The $N_1$-phenyl lower alkyl substituted 2- or 3-phenyl substituted $N_4$-basically substituted 3- or 2-piperazone compounds of Formulas VII or VIII:

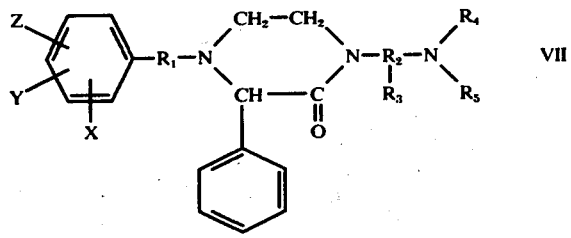

VII

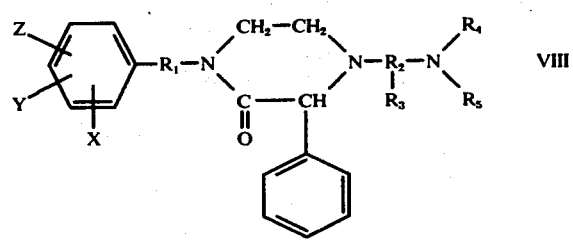

VIII and b. the $N_1$-phenyl lower alkyl substituted 2- or 3-phenyl substituted $N_4$-basically substituted piperazine compounds of Formulas IX and X:

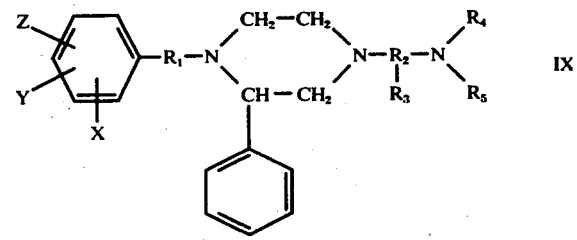

IX

-continued

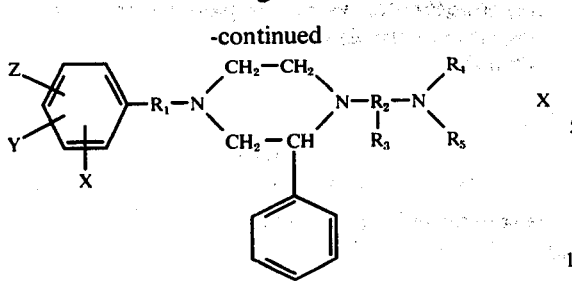

In said Formulas VII to X the symbols $R_1$, $R_2$, $R_3$, $R_4$, $R_5$, X, Y, and Z represent the same substituents as indicated hereinabove.

Especially valuable compounds according to the present invention are compounds of the following Formula XI and XII:

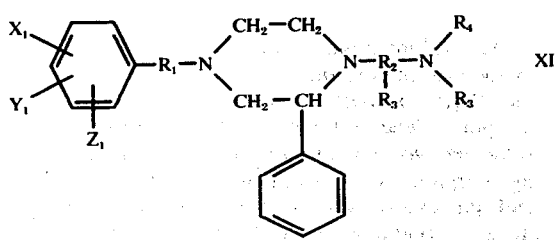

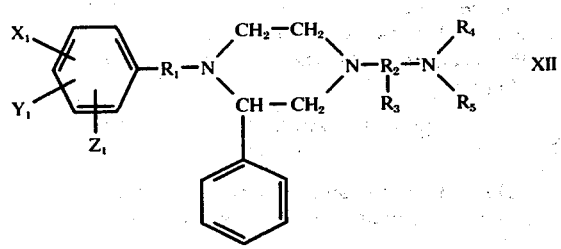

In said Formulas
$X_1$ is hydrogen or lower alkoxy.
$Y_1$ and $Z_1$ are hydrogen, halogen, trifluoromethyl; hydroxyl, lower alkoxy, and phenyl lower alkoxy, whereby $X_1$ is lower alkoxy only if $Y_1$ and $Z_1$ are lower alkoxy;
$R_1$ is lower alkyl with 1 to 3 carbon atoms;
$R_2$ is lower alkyl;
$R_3$ is hydrogen or a saturated five- or six-membered heterocyclic ring, said heterocyclic ring being attached by its heterocyclic nitrogen atom to the lower alkyl $R_2$;
$R_4$ and $R_5$ are lower alkyl or, together with the nitrogen atom to which they are attached, form a saturated five- or six-membered heterocyclic ring.

According to the present invention the 1,4-substituted phenyl piperazine compounds of the above given Formulas have a pronounced effect upon the blood coagulation system. They act upon all processes which play an essential role in the formation of thromboses, such as their coagulation promoting effect due to their power of releasing the thrombocyte factor 3, their coagulation inhibiting effect, and their thrombocytes aggregation and adhesion inhibiting effect. Thus the novel compounds of the present invention or their pharmaceutically acceptable acid addition salts are highly effective anticoagulants. They prolong the clotting time of blood on oral or parenteral administration of the required dose and have been found to inhibit platelet aggregation, such as induced by the addition of adenosine diphosphate, when added to platelet-rich plasma.

The compounds according to the present invention can be administered for their anticoagulant effect over a wide dosage area. For instance, a dosage of about 0.5 mg./kg. to 100 mg./kg. of body weight orally administered daily or on parenteral administration has proved to be highly effective.

The new compounds according to the present invention may find particular application in the treatment of thrombotic disease, especially of the arterial system, for instance, to inhibit thrombosis of the coronary or cerebral arteries.

The following new piperazine compounds according to the present invention have been found to be useful in therapy:
1-(4-chloro benzyl)-2-phenyl-4-(diethylamino ethyl)piperazine
1-(3,4-dichloro benzyl)-2-phenyl-4-(diethylamino ethyl)piperazine;
1-[(4-methoxy phenyl)-ethyl]-2-phenyl-4-(diethylaminoethyl)-piperazine;
1-[3-phenyl propyl-(1)]-2-phenyl-4-(diethylamino ethyl)-piperazine;
1-(4-chloro benzyl)-2-phenyl-4-(piperidino ethyl) piperazine;
1-(4-chloro benzyl)-2-phenyl-4-[1,3-dimorpholino propyl-(2)]piperazine;
1-(4-chloro benzyl)-3-phenyl-4-(diethylamino ethyl) piperazine.

The new piperazine compounds of the above given Formulas are obtained according to the present invention, for instance, by reacting a 1-R-substituted phenyl piperazine of Formula XIII.

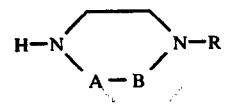

wherein

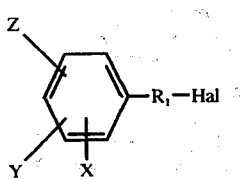

and R represent the above given groups and substituents,
with an aralkyl halogenide of Formula XIV

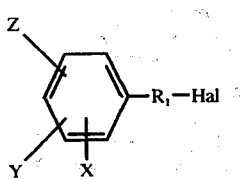

wherein
X, Y, Z, and $R_1$ represent the same substituents and numerals as given hereinabove, while
Hal is halogen.

Another method of producing the 1,4-substituted phenyl piperazine compounds according to the present invention comprises reacting a 1-aralkyl phenyl piperazine of Formula XV.

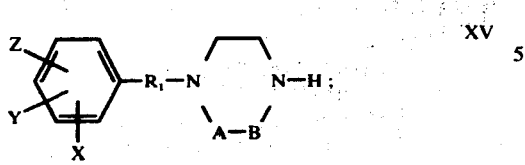

wherein

X, Y, Z, and $R_1$ represent the above given substituents, with a basically substituted alkyl halogenide of Formula XVI Hal—R   XVI wherein Hal is halogen and R represents the above given substituent.

A further method of producing the 1,4-substituted phenyl piperazine compounds according to the present invention comprises reacting a 1-aralkyl phenyl piperazine, substituted in the ω-position by a reactive group Q, preferably by a halogen atom, and having the general Formula XVII

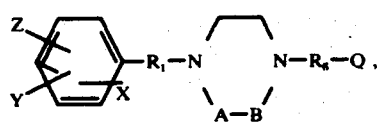

wherein

X, Y, Z, and $R_1$ have the above given meaning, and $R_6$ is lower alkyl, with a corresponding secondary amine of the group consisting of a di-lower alkyl amine, such as dimethylamine, diethylamine, dipropylamine, or with piperidine, morpholine, pyrrolidine, piperazine, 3-ketopiperazine, or a lower N-alkyl piperazine.

If desired, the keto group in the resulting reaction product of Formula V, wherein

is either

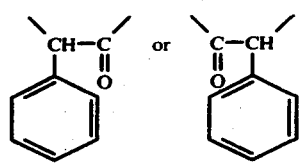

is reduced to the methylene group, so as to yield compounds of Formula V
wherein

represents either

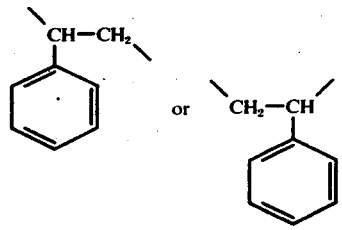

The resulting basically substituted phenyl piperazine compounds of Formula V may be converted, if desired, into their substantially non-toxic, pharmaceutically acceptable acid addition salts by methods well known to the art. Not only physiologically tolerable salt-forming inorganic acids, such as hydrochloric acid, sulfuric acid, phosphoric acid, hydrobromic acid, and others, but also organic acids, such as acetic acid, propionic acid, benzoic acid, salicyclic acid, succinic acid, malonic acid, citric acid, tartaric acid, fumaric acid, and others can be used in the preparation of therapeutically valuable salts.

DESCRIPTION OF THE PREFERRED EMBODIMENTS

The following examples serve to illustrate the present invention without, however, limiting the same thereto.

EXAMPLE 1

1-(4'-Chloro benzyl)-2-phenyl-4-(diethylamino ethyl) piperazine

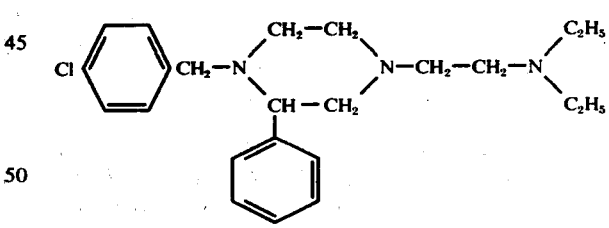

Method A:

1-(4'-Chloro benzyl)-2-phenyl piperazine 44 g. of 1-(4'-chloro benzyl)-2-phenyl-3-keto piperazine obtained according to Example 1, Method A (a) of Application Ser. No. 333,497, are dissolved in 350 cc. of dioxane. The solution is added drop by drop to a suspension of 15 g. of lithium aluminum hydride $LiAlH_4$ in 800 cc. of ether while stirring thoroughly. After addition is completed, the reaction mixture is boiled under reflux for 12 hours. Thereafter, the lithium complex compound is decomposed and excess lithium aluminum hydride is destroyed by successively treating the reaction mixture with 15 cc. of a 15% sodium hydroxide solution, with 15 cc. of water, with 45 cc. of a 15% sodium hydroxide solution, and with 30 cc. of water. The inorganic precipitate is removed by filtration and the filtered solution is evaporated to dryness. The residue is recrystallized from isopropanol. 37 g. of pure white crystals of the melting point 103°–104° C. are obtained.

Method B:

1-(4'-Chloro benzyl)-2-phenyl piperazine 142.4 g. of 1(4'-chloro benzyl)-2-phenyl-3-keto piperazine prepared according to Example 1, Method A (a) of Application Ser. No. 333,497, are suspended in 400 cc. of benzene while stirring vigorously. 800 cc. of a 1.5 molar solution of dibutyl aluminum hydride are then allowed to run slowly to said suspension. Thereby the reaction mixture is caused to boil under reflux. Half an hour after the addition is completed, the mixture is cooled to 5° C. Excess dibutyl aluminum hydride is decomposed by careful addition of water. The precipitated aluminum hydroxide is dissolved in 40% sodium hydroxide solution. The separated organic layer is washed with 40% sodium hydroxide solution and then with water and is freed of its organic solvent by evaporation. The residue is recystallized from 1.5 l. of isopropanol.

Pure white crystals of the melting point 103°–104° C. are obtained in a yield corresponding to the theoretical yield. The resulting compound is identical with the compound obtained according to Method A given hereinabove as is proved by chromatography and infrared spectroscopy.

b. 1-(4'-Chloro benzyl)-2-phenyl-4-(diethylamino ethyl) piperazine 30 g. of the base prepared according to Methods A or B as described hereinabove are dissolved in 100 cc. of toluene. The solution is boiled under reflux with 20 g. of diethylamino ethylchloride and 20 g. of finely pulverized anhydrous potassium carbonate for 8 hours. By treating the reaction mixture with water, separating the toluene layer, extracting the base with hydrochloric acid, setting the base free from its hydrochloride solution by addition of ammonia, and dissolving it in benzene, the base is purified. After distilling off the solvent and repeated distillation in a vacuum, 34 g. of a yellow oil of the boiling point 188°–199° C./0.09 mm. Hg are obtained. Yield: 81% of the theoretical yield.

EXAMPLE 2

1-(3',4'-Dichloro benzyl)-2-phenyl-4-(diethylamino ethyl) piperazine

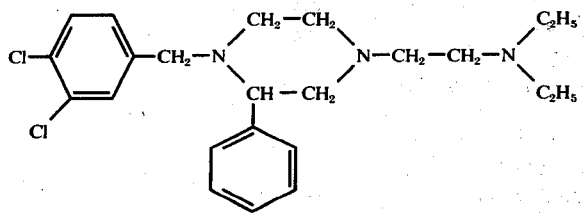

a. 1-(3',4'-Dichloro benzyl)-2-phenyl-3-keto piperazine 140 g. of 2-phenyl-3-keto piperazine are boiled under reflux with 163 g. of 3,4-dichloro benzylchloride in 1,600 cc. of acetone for 6 hours while 330 cc. of triethylamine are added. The hot reaction mixture is filtered to remove precipitated triethyl ammonium chloride and is concentrated by fractional distillation. The resulting crystal fractions are twice recrystallized from 4 l. of 96% ethanol.

162 g. of the above given reaction product of the melting point 195°–208° C. (with decomposition) are obtained. Yield: 52% of the theoretical yield.

b. 1-(3',4'-Dichloro benzyl)-2-phenyl piperazine 132 g. of the keto piperazine prepared as described hereinabove under (a) are dissolved in 200 cc. of dioxane. Said solution is added drop by drop to a suspension of 21 g. of lithium aluminia hydride LiAlH$_4$ in 900 cc. of absolute ether while the suspension is exposed to vibration. After the addition is completed, the mixture is boiled under reflux for 12 hours. Successively 20 cc. of 15% sodium hydroxide solution, 20 cc. of water, 60 cc. of 15% sodium hydroxide solution, and 40 cc. of water are added to the reaction mixture to cause decomposition of the complex compound formed. The filtrate is freed of solvent, the residue is distilled, and a viscous oil, boiling between 170° C./0.02 Torr. and 178° C./0.02 Torr., is obtained. The oil crystallizes on trituration with heptane. It is twice recrystallized from heptane. Yield: 110 g. corresponding to 87% of the theoretical yield.

c. 1-(3',4'-Dichloro benzyl)-2-phenyl-4-diethylamino ethyl) piperazine 40 g. of the piperazine compound prepared according to the method described hereinabove under (b), are boiled under reflux with 18.5 g. of diethylamino ethylchloride in 250 cc. of acetone with the addition of 52 cc. of triethylamine for 12 hours. The triethyl ammonium-chloride formed thereby is filtered off. The resulting solution is concentrated by evaporation. Absolute ethanolic hydrochloric acid is added to the residue. The precipitated hydrochloride is washed with ethanol and is dissolved in water. The base is set free from its aqueous solution by the addition of ammonia and is extracted by means of benzene. After drying over anhydrous potassium carbonate and removing the solvent, 34 g. of a light yellow oil of the boiling point 192° C./0.03 mm. Hg are obtained. The yield is 65% of the theoretical yield.

EXAMPLE 3

1-[(4'-Methoxy phenyl) ethyl]-2-phenyl-4-(diethylamino ethyl) piperazine

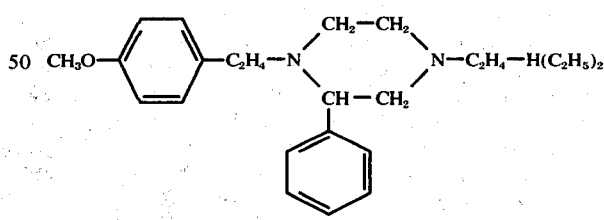

a. 1-[(4'-Methoxy phenyl)ethyl]-2-phenyl-3-keto piperazine 140 g. of 2-phenyl-3-keto piperazine, 148.5 g. of 4-methoxy phenyl ethylchloride, and 330 cc. of triethylamine in 1.6 l. of acetone are boiled under reflux for 12 hours. The acetone is distilled off. 300 cc. of dimethylformamide are added to the residue and the mixture is heated on the water bath for 36 hours. The major part of the dimethylformamide is distilled off in a vacuum. About 500 cc. of acetone and 150 cc. of triethylamine are added to the residue. The mixture is freed of triethylammoniumchloride by filtration while still boiling, and is cooled. After again distilling off the solvent, the remaining crystals are washed with petroleum ether and are triturated with water. The resulting solution is again filtered. On rendering the solution alkaline, the reaction product is precipitated initially in oily form. It crystallizes very rapidly. After recrystallizing the crystals three times from isopropanol pure white crystals of the melting point 142°–147° C. (with decomposition) are obtained. The yield is 110 g. corresponding to 44.7 % of the theoretical yield.

When carrying out the reaction from the beginning on in a mixture of dimethylformamide and triethylamine, the yield is lower than when proceeding as described hereinabove. This is due to formylation reaction taking place thereby.

b. 1-[(4'-Methoxyphenyl)-ethyl]-2-phenyl piperazine 29 g. of the keto piperazine prepared as described hereinabove under (a), are dissolved in 200 cc. of absolute dioxane. A suspension of 8 g. of lithium aluminum hydride LiAlH₄ in 700 cc. of absolute ether is added drop by drop to said solution while stirring vigorously. Thereafter, the mixture is boiled under reflux for 12 hours. After decomposing the reaction mixture by successive addition of 10 cc. of 15 % sodium hydroxide solution, 10 cc. of water, 30 cc. of 15 % sodium hydroxide solution, and finally of 20 cc. of water in the order given, the mixture is freed from the precipitated inorganic salts by filtration and the filtrate is concentrated by evaporation. Ethanolic hydrochloric acid is added to the residue and the hydrochloride precipitated thereby is filtered off by suction. The base is set free from the hydrochloride by the addition of sodium hydroxide solution. 23 g. of a viscous oil are obtained. The oil crystallizes after standing for some time. It has a boiling point of 180°–185° C./0.01 mm. Hg. The yield is 83 % of the theoretical yield.

c. 1-[(4'-Methoxy phenyl)-ethyl]-2-phenyl-4-(diethylamino ethyl) piperazine 18 g. of the base obtained as described hereinabove under (b) are boiled under reflux with 30 g. of triethylamine and 12 g. of diethylamino ethylchloride in 120 cc. of acetone for 15 hours. The reaction solution is cooled, filtered, and freed of the solvent by concentration by evaporation. The residue is dissolved in dilute hydrochloric acid. The base is set free from its hydrochloride solution by the addition of ammonia, is extracted with benzene, and the benzene extract is again freed of its solvent. A mixture of acetone in ethanolic hydrochloric acid is added to the residue. The precipitated hydrochloride is filtered off by suction. The base is again set free from its hydrochloride by the addition of ammonia and is distilled in a vacuum. 17 g. of a viscous oil of the boiling point 215° C./0.002 mm. Hg are obtained. The yield is 70 % of the theoretical yield.

EXAMPLE 4

1-[3'-Phenyl propyl-(1)]-2-phenyl-4-(diethylamino ethyl) piperazine

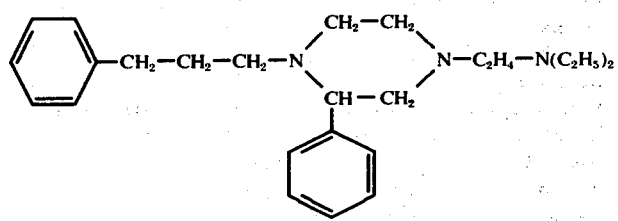

a. 1-[3'-Phenyl propyl-(1)]-2-phenyl-3-keto piperazine 140 g. of 2-phenyl-3-keto-piperazine and 135 g. of 3-phenyl propylchloride(1) are heated on the water bath in 350 cc. of dimethylformamide with the addition of 330 cc. of triethylamine for 48 hours. The major portion of the dimethylformamide and the triethylamine are distilled off in a vacuum. The residue is dissolved in 2 l. of acetone. 150 cc. of triethylamine are added to said acetone solution. The mixture is boiled under reflux for 10 minutes. The solution is then cooled to 30° C. and is freed from triethyl ammoniumchloride by filtration. The keto-piperazine crystallizes from the resulting filtrate on cooling in a mixture of ice and sodium chloride. The crystals are purified by recrystallization from isopropanol and 50 % ethanol. 110 g. of white crystals of the melting point 114°–116° C. are obtained. The yield is 47 % of the theoretical yield.

b. 1-[3'-Phenyl propyl-(1)]-2-phenyl piperazine 43 g. of the keto-piperazine obtained as described hereinabove under (a) are dissolved in 200 cc. of dioxane and are reduced by the addition of 10 g. of lithium aluminum hydride LiAlH₄ suspended in 800 cc. of ether as described in the preceding examples. After decomposing the reaction mixture and recovering the base by purification via its hydrochloride, 30 g. of a viscous oil of the boiling point 155°–160° C./0.01 mm. Hg are obtained. The yield is 73 % of the theoretical yield.

c. 1-[3'-Phenyl propyl-(1)]-2-phenyl-4-(diethylamino ethyl) piperazine 23 g. of the base prepared as described hereinabove under (b) are boiled under reflux with 13.5 g. of diethylamino ethylchloride, 35 cc. of triethylamine, and 150 cc. of acetone for 10 hours. After recovering the base as described in the preceding examples and purifying it via its hydrochloride, 22 g. of a colorless oil of the boiling point 187°–189° C./0.01 mm. Hg are obtained. The yield is 70.5 % of the theoretical yield.

EXAMPLE 5

1-(4'-Chloro benzyl)-2-phenyl-4-(piperidino ethyl) piperazine

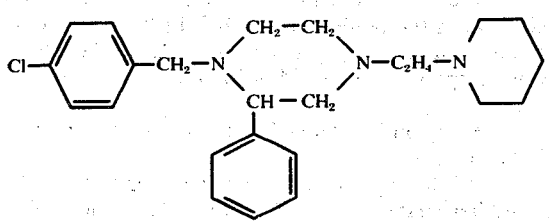

31 g. of 1-(4'-chloro benzyl)-2-phenyl piperazine prepared according to Example B), 25 g. of piperidino ethylchloride, 20 g. of triethylamine, and 250 cc. of acetone are boiled under reflux for 18 hours. The filtered reaction solution is freed of its solvent by concentration by evaporation. The residue is dissolved in benzene. The benzene solution is washed with water. After drying and distilling off the solvent, the base is obtained in the form of a viscous, yellow oil on distillation at 210° C./0.06 Torr. The oil crystallizes on trituration with isopropanol. After three recrystallizing the crystals from n-heptane (41 g. of yellow crystals of the melting point 85°–87° C.) are obtained. The yield is 95 % of the theoretical yield.

In place of acetone there may also be used other solvents, for instance, benzene, toluene, or xylene and, in place of triethylamine, for instance, pyridine, dimethylaniline, potassium carbonate, sodium amide or sodium hydride.

In a similar manner as described in Example 6 are obtained:

1-(4'-Chloro benzyl)-2-phenyl-4-pyrrolidino ethyl) piperazine, boiling point 200°–205° C./0.05 mm. Hg; melting point of the hydrochloride 254°–258° C. (decomposition), by reaction of 1-(4'-chloro benzyl)-2-phenyl piperazine and pyrrolidino ethyl chloride.

1-(4'-Chloro benzyl)-2-phenyl-4-[4'-methyl piperazino ethyl-(1)]piperazine, boiling point 215°–217° C./0.005 mm. Hg; melting point of the hydrochloride 252°–270° C. (decomposition), by reaction of 1-(4'-chloro benzyl)-2-phenyl piperazine and 1-(3-chloro ethyl)-4-methyl piperazine.

EXAMPLE 6

1-(4'-Chloro benzyl)-2-phenyl-4-[1'',3''-dimorpholino propyl(2'')]-piperazine

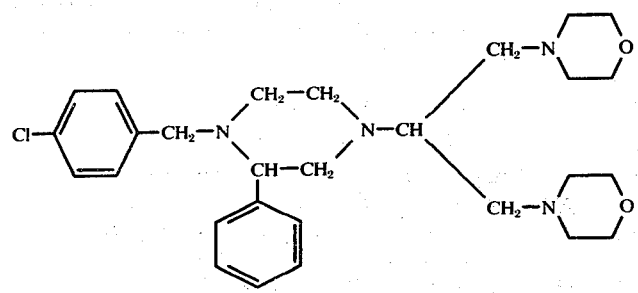

31 g. of 1-(4'-chloro benzyl)-2-phenyl piperazine prepared according to Example B, 52 g. of 1,3-dimorpholino propylchloride-(2), prepared by chlorinating 1,3-dimorpholino propanol-(2), 25 g. of triethylamine, and 250 cc. of acetone are boiled under reflux for 48 hours. The base remaining after filtration and evaporation of the solvent is purified by dissolving it in hydrochloric acid and setting it free from its hydrochloride solution by the addition of ammonia. The base is dissolved in benzene, and the benzene solution dried over anhydrous potassium carbonate. After distilling off the solvent, the residue is distilled in a vacuum of 0.1 Torr. The first fraction distilling over at a temperature up to 110° C. consists mainly of unreacted dimorpholino propylchloride. The remaining residue is dissolved in petroleum ether and is separated from undissolved matter by filtration after cooling. The solvent is distilled off and the remaining compound is purified by distillation in a vacuum. 34 g. of an oil of the boiling point 230° C./0.001 mm. Hg are obtained. The oil solidifies on standing.

EXAMPLE 7

1-(4'-Chloro benzyl)-3-phenyl-4-(diethylamino ethyl) piperazine

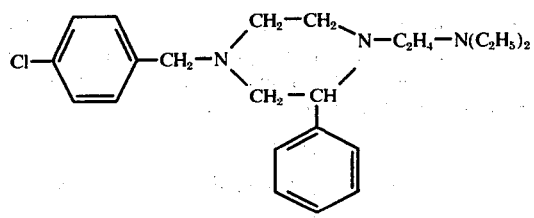

a. 1-(Diethylamino ethyl)-2-phenyl piperazine 1-(Diethylamino ethyl)-2-phenyl-3-keto piperazine is prepared by reacting $N_1$-(diethylamino ethyl) ethylenediamine with α-chloro phenyl acetylchloride and isolating the above mentioned reaction product from the resulting mixture of isomers.

89 g. of said keto piperazine dissolved in 200 cc. of dioxane are added drop by drop to a suspension of 20 g. of lithium aluminum hydride $LiAlH_4$ in 800 cc. of ether. After addition of the keto piperazine, the reaction mixture is boiled under reflux for 6 hours. It is then decomposed by successively adding 20 cc. of 15% sodium hydroxide, 20 cc. of water, 60 cc. of 15% sodium hydroxide solution, and finally 40 cc. of water. The filtered solution is concentrated by evaporation and the residue is distilled in a vacuum. The resulting oil which distills at a temperature between 102° C. and 115° C./0.05 mm. Hg, is dissolved in benzene and is extracted therefrom by shaking in 10% hydrochloric acid. The base is set free from its hydrochloride solution by the addition of 10% sodium hydroxide solution and is repeatedly distilled in a vacuum. An almost colorless oil of the boiling point 114°–117° C./0.07 mm. Hg is obtained. The yield corresponds to the theoretical yield. The compound contains a small amount of 3-phenyl-1-(diethylamino ethyl) piperazine.

b. 1-(4'-Chloro benzyl)-3-phenyl-4-diethylamino ethyl) piperazine 26 g. of the base prepared as described hereinabove under (a) are boiled under reflux with 17.7 g. of 4-chloro benzylchloride and 42 cc. of triethylamine in 200 cc. of acetone for 10 hours. After filtration and distilling off the solvent, the base is purified in the manner described hereinabove via its hydrochloride and is set free from said hydrochloride by the addition of ammonia. The residue is freed of the solvent and is dissolved in acetic acid ethyl ester. The hydrochloride is precipitated from said solution by the addition of absolute ethanolic hydrochloric acid. The hydrochloride is recrystallized from acetic acid ethyl ester. The base is set free from said hydrochloride by means of ammonia and is distilled in a vacuum. An almost colorless oil of the boiling point 180° C./0.01 mm. Hg is obtained. The yield is 30 g. corresponding to 78% of the theoretical yield.

This compound can be distinguished by means of its infrared spectrum from the isomeric 1-(4'-chloro benzyl)-2-phenyl-4-(diethylamino ethyl) piperazine by directly comparing both compounds.

EXAMPLE 8

1-(Diethylamino ethyl)-2-phenyl-4-(p-ethoxy benzyl) piperazine

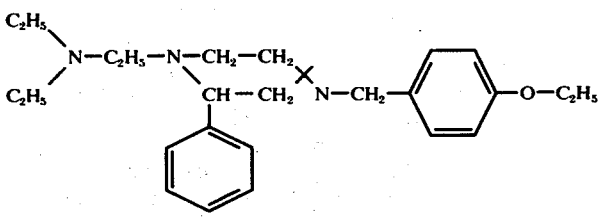

(a) 1-Diethylamino ethyl-2-phenyl-3-keto piperazine 144 g. of 2-phenyl-3-keto piperazine are boiled under reflux with 121 g. of diethylamino ethylchloride, 340 cc. of triethylamine, and 1600 cc. of acetone for 24 hours. The cooled solution is filtered to remove triethylamine hydrochloride and the filtrate is evaporated to dryness. The residue is dissolved in water, 40% sodium hydroxide solution is added thereto, and the oil which forms as upper layer, is extracted with benzene. The benzene solution is dried over anhydrous potassium carbonate, the benzene is removed by distillation, and the residue is distilled in a vacuum. A light yellow, viscous oil of the boiling point 175° C./0.05 mm. Hg is obtained. The oil is twice recrystallized from n-heptane. 145 g. of the above mentioned compound melting at 53°–56° C. are obtained. The yield is 64% of the theoretical yield.

b. 1-Diethylamino ethyl-2-phenyl piperazine 89 g. of the keto piperazine prepared as described hereinabove under (a), are dissolved in 200 cc. of absolute dioxane. The solution is added to a suspension of 20 g. of lithium aluminum hydride $LiAlH_4$ in 800 cc. of absolute ether while exposing the mixture to vibration. After addition of the keto piperazine solution is completed, the reaction mixture is boiled under reflux for 6 hours. Thereafter it is decomposed by successive treatment with 21 cc. of 15% sodium hydroxide solution, 21 cc. of water, 63 cc. of 15% sodium hydroxide solution, and 42 cc. of water. The decomposed reaction mixture is filtered, the solvent is removed by distillation, and the residue is distilled in a vacuum. 65 g. of a light yellow oil of the boiling point 114°–117° C./0.05 mm. Hg are obtained. This oil corresponds to the above given compound. The yield is 77 % of the theoretical yield.

c. 1-Diethylamino ethyl-2-phenyl-4-(p-ethoxy benzyl) piperazine 40 g. of the piperazine derivative prepared as described hereinabove under (b) are boiled under reflux with 27 g. of p-ethoxy benzylchloride in 400 cc. of acetone with the addition of 50 cc. of triethylamine for 12 hours. The triethyl ammonium hydrochloride formed thereby is filtered off. The acetone is removed by distillation. The residue is dissolved in benzene and the base is dissolved therefrom in the form of its hydrochloride by extraction with dilute hydrochloric acid. The base is set free from its hydrochloride solution by the addition of ammonia and is extracted with benzene. The benzene solution is dried over anhydrous potassium carbonate. The solvent is distilled off and the residue is distilled in a vacuum. 39 g. of a light yellow viscous oil of the boiling point 200° C/0.05 mm. Hg are obtained. The yield is 64% of the theoretical yield.

EXAMPLE 9

1-Diethylamino ethyl-3-phenyl piperazine

1-Diethylamino ethyl-2-keto-3-phenyl piperazine prepared according to Example 1 B (a) of application Ser. No. 333,497, is reduced by following the procedure described hereinabove in Example 7 (a) whereby, in place of 1-diethylamino ethyl-3-keto-2-phenyl piperazine, the equimolecular amount of said 1-diethylamino ethyl-2-keto-3-phenyl piperazine is reduced. The resulting 3-phenyl piperazine compound is obtained in the form of a light yellow oil boiling at 102° C./0.02 mm. Hg.

EXAMPLE 10

1-Benzyloxy benzyl-2-phenyl piperazine

1-Benzyloxy benzyl-2-phenyl-3-keto piperazine prepared according to Example 12, is reduced by following the procedure described hereinabove in Example 8 (a) whereby, in place of 1-diethylamino ethyl-3-keto-2-phenyl piperazine, the equimolecular amount of said 1-benzyloxy benzyl-2-phenyl-3-keto piperazine is used. The resulting 2-phenyl piperazine compound is obtained in the form of white crystals melting at 140–141° C.

EXAMPLE 11

1-(3',4',5'-Trimethoxy benzyl)-2-phenyl piperazine 1-(3',4',5'-Trimethoxy benzyl)-2-phenyl-3-keto piperazine prepared according to Example 13, is reduced by following the procedure described hereinabove in Example 8 (a) whereby, in place of 1-diethylamino ethyl-3-keto-2-phenyl piperazine, the equimolecular amount of said 1-(3',4',5'-trimethoxy benzyl-2-phenyl-3-keto piperazine is used. The resulting 2-phenyl piperazine compound is obtained in the form of a yellow oil boiling at 185-195° C./0.08 mm. Hg.

EXAMPLE 12

1-[3'-(4''-Methoxy phenyl) propyl(1)]-2-phenyl piperazine

1-[3'-(4''-Methoxy phenyl) propyl(1)]-2-phenyl-3-keto piperazine prepared according to Example 14, is reduced by following the procedure described hereinabove in Example 8 (a) whereby, in place of 1-diethylamino ethyl-3-keto-2-phenyl piperazine, the equimolecular amount of said 1-[3'-(4''-methoxy phenyl) propyl(1)]-2-phenyl-3-keto piperazine is used. The resulting 2-phenyl piperazine is obtained in the form of a light yellow oil boiling at 176° C./0.05 mm. Hg.

EXAMPLE 13

1-(4'-Chloro benzyl)-3-phenyl-4-diethylamino ethyl piperazine 1-(4'-Chloro benzyl)-2-keto-3-phenyl-4-diethylamino ethyl piperazine prepared according to Example 10, is reduced by following the procedure described hereinabove in Example 8 (a) whereby, in place of 1-diethylamino ethyl-3-keto-2-phenyl piperazine, the equimolecular amount of said 1-(4'-Chloro benzyl)-2-keto-3-phenyl-4-diethylamino ethyl piperazine is used. The resulting 3-phenyl piperazine compound is obtained in the form of a light yellow oil boiling at 180° C./0.01 mm. Hg.

EXAMPLE 14

1-(3',4'-Dichloro benzyl)-2-phenyl-4-dimethylamino ethyl piperazine 1-(3',4'-Dichloro benzyl)-2-phenyl piperazine prepared according to Example 3 (b), is alkylated by following the procedure described in Example 3 (c), whereby, in place of the diethylamino ethylchloride, the equimolecular amount of dimethylamino ethylchloride is used. The resulting reaction product is obtained in the form of a light yellow oil boiling at 190° C./0.01 mm. Hg.

EXAMPLE 15

1-(3',4'-Dichloro benzyl)-2-phenyl-4-morpholino ethyl piperazine 1-(3',4'-Dichloro benzyl)-2-phenyl piperazine prepared according to Example 3 (b), is akylated by following the procedure described in Example 3 (c) whereby, in place of diethylamino ethylchloride, the equimolecular amount of morpholino ethylchloride is used. The resulting reaction product is obtained in the form of a light yellow oil boiling at 230° C./0.04 mm. Hg.

EXAMPLE 16

1-(3',4'-Dichloro benzyl)-2-phenyl-4-diethylamino propyl piperazine 1-(3',4'-Dichloro benzyl)-2-phenyl piperazine prepared according to Example 2 (b), is alkylated by following the procedure described in Example 2 (c) whereby, in place of the diethylamino ethylchloride, the equimolecular amount of diethylamino propylchloride is used. The resulting reaction product is obtained in the form of a light yellow oil boiling at 210° C./0.04 mm. Hg.

EXAMPLE 17

1-(4'-Benzyloxy benzyl)-2-phenyl-4-diethylamino ethyl piperazine 1-(4'-Benzyloxy benzyl)-2-phenyl piperazine prepared according to Example 10, is alkylated by means of diethylamino ethylchloride by following the procedure described in Example 2 (c). The resulting reaction product is obtained in the form of a light yellow oil boiling at 235° C./0.01 mm. Hg.

EXAMPLE 18

1-(3',4',5'-Trimethoxy benzyl)-2-phenyl-4-diethylamino ethyl piperazine 1-(3',4',5'-Trimethoxy benzyl)-2-phenyl piperazine prepared according to Example 11, is alkylated by means of diethylamino ethylchloride by following the procedure described in Example 2 (c). The resulting reaction product is obtained in the form of yellow oil boiling at 200° C./0.03 mm. Hg.

EXAMPLE 19

1-[3'-(4''-Methoxy phenyl) propyl(1)]-2-phenyl-4-diethylamino ethyl piperazine

1-[3'-(4''-Methoxy phenyl) propyl(1)]-2-phenyl piperazine prepared according to Example 12, is alkylated by means of diethylamino ethylchloride by following the procedure described in Example 2 (c). The resulting reaction product is obtained in the form of a yellow oil boiling at 130°-190° C./0.01 mm. Hg.

EXAMPLE 20

1-(4'-Ethoxy benzyl)-3-phenyl-4-diethylamino ethyl piperazine

1-Diethylamino ethyl-2-phenyl piperazine prepared according to Example 7 (a), is reacted with 4-ethoxy benzylchloride by following the procedure described in Example 7 (b) and using, in place of 4-chloro benzylchloride, the equimolecular amount of 4-ethoxy benzylchloride. The resulting reaction product is obtained in the form of a yellow oil boiling at 200° C./0.05 mm. Hg.

EXAMPLE 21

1-(4'-Chloro benzyl)-2-phenyl-4-(diethylamino ethyl) piperazine

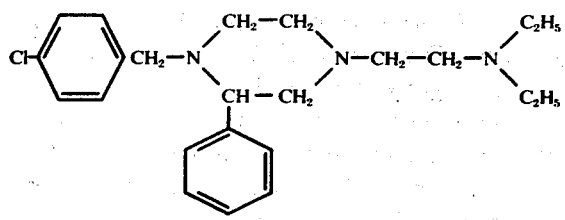

A. 1-(4-Chloro benzyl)-2-phenyl-4-(β-hydroxy ethyl) piperazine

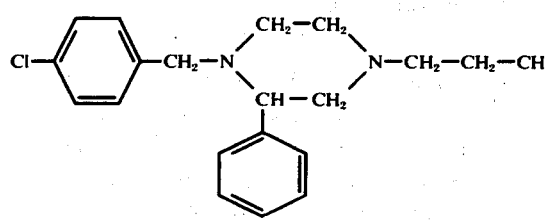

a. 30 g. of 1-(4'-chloro benzyl)-2-phenyl piperazine, prepared according to Example 1 A), 20 g. of ethylene chlorohydrin, 20 g. of triethylamine and 250 cc. of methyl ethyl ketone are boiled under reflux for 24 hours. After cooling, the triethylamine hydrochloride formed thereby is removed by filtration, the filtrate is evaporated in a vacuum, the residue is dissolved in benzene, the benzene solution is washed with water and dried over anhydrous potassium carbonate. The benzene is removed by distillation and the residue is distilled in a vacuum. A yellow, viscous oil of the boiling point 195° C./0.01 mm. Hg is obtained. The oil is twice recrystallized from isopropanol and then from n-heptane. Melting point 91–94° C.; yield 22 g.

b. A mixture of 28.6 g. of 1-(4'-chloro benzyl)-2-phenyl piperazine, 6.0 g. of ethylene oxide and 200 cc. of methanol is let standing for 4 days in a closed flank at room temperature. Then the methanol is distilled off and the residue is distilled at 193° C./0.01 mm. Hg. The base is twice recrystallized from n-heptane, whereby a product having a melting point of 91°–94° C. is obtained. Yield 19 g.

c. 50 g. of 1-(4'-chloro benzyl)-2-phenyl piperazine are dissolved in 100 cc. of dioxane. To this solution are added 31 g. of acetylglycolic acid chloride, dissolved in 50 cc. of dioxane. The mixture boiled for 2 hours under reflux. The dioxane is distilled off in a vacuum and the residue is dissolved in benzene; the benzene solution is washed with an aquous 10% sodium hydroxide solution and is dried over anhydrous potassium carbonate. The solvent is distilled off and the residue is recrystallized three times from isopropanol. Melting point 136°–137° C.; yield 46 g.

44 g. of the piperazine derivative obtained as above are dissolved in 120 cc. of absolute dioxane and added slowly drop to drop to a suspension of 10 g. of LiAlH₄ in 700 cc. of absolute ether. The mixture is boiled under reflux for 2.5 hours. It is then decomposed by adding 10 cc. of 15% sodium hydroxide solution, 10 cc. of water, 30 cc. of 15% sodium hydroxide solution and 20 cc. of water. The precipitated inorganic material is separated by filtration and the solvent is distilled in a vacuum. The residue is recrystallized three timed from n-heptane. The obtained compound has a melting point of 91°–94° C. Yield 17 g.

B. 1-(4'-Chloro benzyl)-2-phenyl-4-(2-chloro ethyl)-piperazine hydrochloride.

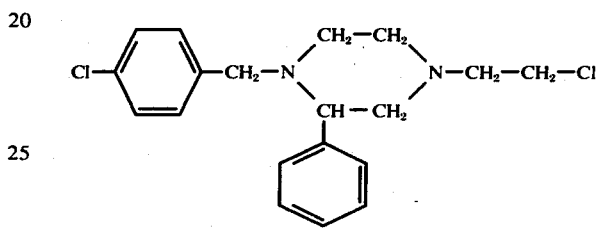

24 g. of 1-(4'-chloro benzyl)-2-phenyl-4-(β-hydroxy ethyl) piperazine are dissolved in 150 cc. of chloroform and added drop by drop to a solution of 15 g. of thionyl chloride in 150 cc. of chloroform. The mixture is boiled under reflux for 5 hours and the solvent is removed in a vacuum by heating the mixture in a water bath. Excess of absolute ethanolic hydrochloric acid is added and the remaining acid is distilled off. The crystalline residue obtained is recrystallized from absolute ethanol. Melting point 178°–195° C. (dec.); yield 30 g.

C. 1-(4'-Chloro benzyl)-2-phenyl-4-(diethylaminoethyl) piperazine.

20 g. of 1-(4'-chloro benzyl)-2-phenyl-4-(β-chloro ethyl) piperazine hydrochloride, 14 g. of diethylamine and 200 cc. of acetone are boiled under reflux for 12 hours. After cooling, the precipitated diethylamino hydrochloride is filtered off with suction and the solvent of the filtrate is evaporated in a vacuum. The residue is distilled in a vacuum. 15 g. of a light yellow oil having a boiling point of 190° C./0.06 mm. Hg are obtained. This product is identical with the product as obtained according to Example 1 B.

EXAMPLE 22

1-(4'-Chloro benzyl)-2-phenyl-4-[(4''-methyl)-piperazino ethyl-(1)] piperazine.

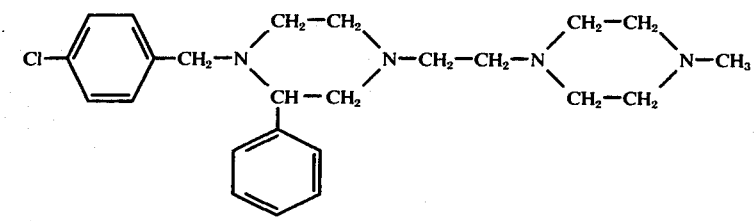

47 g. of 1-(4'-chloro benzyl)-2-phenyl-4-(β-chloro ethyl) piperazine hydrochloride, 16.5 g. of N-methyl piperazine, 75 cc. of triethylamine and 300 cc. of methyl ethyl ketone are boiled under reflux for 12 hours. After cooling the precipitated triethylamino hydrochloride is filtered off with suction and the solvent is distilled off in a vacuum. The residue is dissolved in benzene, the benzene solution is washed with water and dried over anhydrous potassium carbonate. The solvent is distilled off and the residue is disssolved in absolute ethanol. Absolute ethanolic hydrochloric acid is added to precipitate the hydrochloride salt. After cooling the precipitation is separated by filtration, washed with absolute ethanol and dried. Melting point 250°–269° C. (decomposition). To obtain the free base the hydrochloride is dissolved in water and the base is set free from its hydrochloride solution by the addition of ammonia and extracted with benzene. The benzene solution is dried over anhydrous potassium carbonate, the solvent is distilled off and the residue is distilled in a vacuum. Boiling point 220–223° C./0.01 mm. Hg. Yield 30 g.

EXAMPLE 23

1-(4'-Chloro benzyl)-2-phenyl-4-[(3''-keto)piperazino ethyl-(1'')] piperazino.

25 g. of 1-(4''-chloro benzyl)-2-phenyl-4-(β-chloro ethyl) piperazine hydrochloride, 7.3 g. of mono keto piperazine, 200 cc. of methyl ethyl ketone and 200 cc. of triethylamine are boiled for 24 hours under reflux. The precipitated triethylamine hydrochloride is filtered off with suction. Then, the solvent is evaporated, the residue is dissolved in benzene and the benzene solution is washed with water and dried over anhydrous potassium carbonate. The solvent is distilled off and the residue is distilled at 230°–250° C./0.06 mm. Hg (minor decomposition). The distilled product is dissolved in ether, washed with 0.5N hydrochloric acid. The extract obtained with the diluted hydrochloric acid is treated with carbon aand after filtration, the base is set free from said solution by use of ammonia. The base is dissolved in benzene, dried over anhydrous potassium carbonate and after evaporation of the solvent, the residue is distilled at 220°–230° C. (air bath temperature)/0.005 mm. Hg. A very viscous, brownish oil is obtained.

The acid addition salts of the bases according to the present invention are prepared in a manner known per se. For instance, anhydrous ethanolic hydrochloric acid is added to the base whereby the hydrochloride precipitates and is isolated by filtration. Or the base is triturated with the equimolecular amount of the respective acid either as such or in aqueous solution or in solution in an organic solvent and, if required, evaporating the solvent.

Specific procedures to prepare the acid addition salts are the following:

To prepare the hydrochlorides, the bases are dissolved in absolute ethanol and an equimolecular amount of abslute ethanolic hydrochloric acid is added. After cooling, the precipitated hydrochloride is separated by filtration and recrystallised from absolute ethanol or isopropanol.

The succinates or fumarates, respectively, may be obtained using an equimolar amount succinic acid or fumaric acid, respectively, which is added and to the base dissolved in acetone. After boiling under reflux, e.g. for 2 hours, the mixture is cooled and the precipitated salts are separated. The so obtained salts are pure for analysis. In case that the fumarates or succinates, respectively, are not separated from the mixture in crystalline form, the solvent is evaporated and the remaining syrup is triturated to induced crystallization. Recrystallization may be effected by use of ethyl acetate.

To prepare the sulfates, the base is dissolved in absolute ethanol and an equimolecular amount of dilute sulfuric acid is added. The obtained sulfates may be recrystallized from ethanol.

The preparation of the phosphates may be effected by dissolution of the base in absolute ethanol, and addition of an equimolecuar amount of dilute phosphoric acid. The phosphate may be precipitated by use of acetic acid ethyl ester and may be recrystallized by use of isopropanol.

The following acid addition salts have been prepared and isolated:

| Example | Base | Acid addition salt | Melting point |
|---|---|---|---|
| 24 | 1-(4'-Chloro benzyl)-2-phenyl-4-diethylamino ethyl piperazine | Dihydrochloride | 255–1270° C. with decomposition |
| 25 | 1-(3',4'-Dichloro benzyl)-2-phenyl-4-diethylamino ethyl piperazine | Dihydrochloride | 220–222° C. |
| 26 | 1-(3',4'-Dichloro benzyl)-2-phenyl-4-diethylamino ethyl piperazine | o-Phosphate | 220–226° C. |
| 27 | 1-(3',4'-Dichloro benzyl)-2-phenyl-4-diethylamino ethyl piperazine | Sulfate | 210–214° C. |
| 28 | 1-(4'-Chloro benzyl)-2-phenyl-4-piperidino ethyl piperazine | Succinate | 156–158° C. |
| 29 | 1-(4'-Chloro benzyl)-2-phenyl-4-piperidino ethyl piperazine | Fumarate | 190° C. sublimates 250–251° C. with decomposition |
| 30 | 1-[(4'-Methoxy phenyl)ethyl]-2-phenyl-4-diethylamino ethyl piperazine | Hydrochloride | 190–201° C. |
| 31 | 1-[3''-Phenyl propyl(1)]-2-piperazine | Hydrochloride | 185–192° C. |
| 32 | 1-(4'-Chloro benzyl)-3-phenyl-4-diethylamino ethyl piperazine | Hydrochloride | 241–255° C. with decomposition |
| 33 | 1-(4'-Chloro benzyl)-2-phenyl- | Succin- | 95–101° C. |

| Ex-ample | Base | Acid addition salt | Melting point |
|---|---|---|---|
| | 4-diethylamino ethyl piperazine | ate | |

EXAMPLE 34

4-Diethylaminoethyl-3-phenyl-1-o-hydroxy benzyl) piperazine

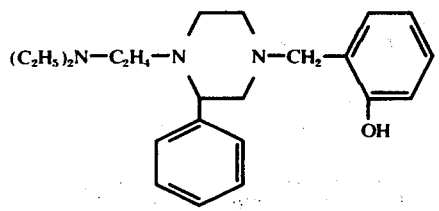

a. 4-Diethylaminoethyl-3-phenyl-1-(o-acetoxy benzoyl)piperazine is prepared by boiling under reflux 15 g. of 1-diethylaminoethyl-2-phenyl-piperazine dissolved in 100 ml. of methyl ethyl ketone with 11 g. of acetyl salicyclic acid chloride dissolved in 50 ml. methyl ethyl ketone, for 6 hours. The solvent is removed by distillation. The residue is dissolved in water. The aqueous solution is extracted with benzene. Ammonia is added to the aqueous layer until its reaction is alkaline and the thus precipitated oil is extracted with benzene. The benzene extract is dried by means of potassium carbonate and the benzene is distilled off. The residue is distilled in a vacuum. Boiling point: 190° C./0.01 mm. (bath temperature). Light yellow, viscous oil.

b. 4-Diethylaminoethyl-3-phenyl-1-(o-hydroxy benzoyl) piperazine is obtained by dissolving the reaction product prepared as described hereinabove under (a) in 100 ml. of dilute hydrochloric acid (2 : 100). The solution is heated to 50° C. for one hour an is then rendered alkaline by the addition of ammonia. The precipitated viscous product is extracted with benzene, the benzene solution is dried by means of potassium carbonate. The benzene is removed by distillation and the residue is distilled in a vacuum. Boiling point: 180° C./0.001 mm. (bath temperature). Light yellow, vitreous product.

c. 4-Diethylaminoethyl-3-phenyl-1-(o-hydroxy benzyl) piperazine is obtained by dissolving 40 g. of 4-diethylaminoethyl-3-phenyl-1-(o-hydroxy benzoyl) piperazine in 150 ml. of dioxane and slowly adding said solution to a suspension of 6 g. of lithium aluminum hydride in 800 ml. of absolute ether. The reaction mixture is boiled under reflux for two hours. The resulting complex compound is decomposed by a treatment with 5 ml. of 15% sodium hydroxide solution followed by 5 ml. of water, 15 ml. of 15% sodium hydroxide solution, and finally 10 ml. of water. The resulting precipitate is filtered off and the solvent is distilled off from the filtrate. The residue is distilled in a vacuum. Boiling point: 180° C./0.001 mm. (bath temperature). Yellow oil.

EXAMPLE 35

1-(p-Hydroxy benzyl)-2-phenyl-4-diethylaminoethyl piperazine

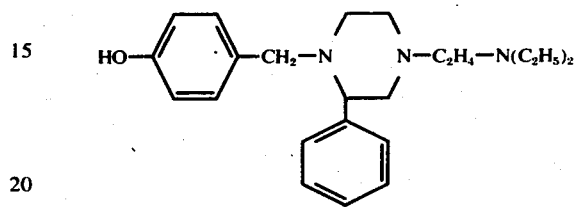

a. 1-(4-Benzyloxy benzyl)-2-phenyl-3-keto piperazine is obtained by boiling under reflux 48 g. of 4-benzyloxybenzyl chloride, 35 g. of 2-phenyl-3-keto piperazine, 500 ml. of acetone, and 50 ml. of triethylamine for 14 hours. Thereafter, the acetone is distilled off and the residue is treated with water. The precipitated crystals are filtered of and are recrystallized from dioxane and thereafter from a mixture of dimethylformamide and water (1 : 1). Melting point: 207°–211° C. White crystals.

b. 1-(4-Benzyloxybenzyl)-2-phenyl piperazine is obtained by suspending 39 g. of the compound prepared according to (a) hereinabove in 150 ml. of dioxane. The suspension is added to a suspension of 10 g. of lithium aluminum hydride (LiAlH$_4$) in 900 ml. of ether. The resulting mixture is boiled under reflux for two hours. The complex compound formed thereby is decomposed by treatment with 10 ml. of 15% sodium hydroxide solution, followed by a treatment with 10 ml. of water, 30 ml. of 15% sodium hydroxide solution, and finally with 20 ml. of water. The decomposed mixture is filtered. The filter residue is discarded. The filtrate is evaporated to dryness and the evaporation residue is recrystallized from dioxane. melding point: 140°–141° C., white crystals.

c. 1-(4-Benzyloxybenzyl)-2-phenyl-4-diethylaminoethyl piperazine is obtained by boiling under reflux 25 g. of the compound prepared according to (b) hereinabove with 10.5 g. of diethylaminoethyl chloride, 30 ml. of triethylamine. and 200 ml. of acetone for six hours. The precipitated triethylamine hydrochloride is filtered off. The acetone is distilled of and the residue is dissoved in benzene. The benzene solution is extracted with dilute hydrochloric acid (1 : 10). The acid solution is made alkaline by the addition of ammonia and the precipitated oil is extracted with benzene. After distilling off the benzene, the residue is distilled in a vacuum. Boiling point: 235° C./0.01 mm. Yellow oil.

d. 1-(p-Hydroxybenzyl)-2-phenyl-4-diethylamino ethyl piperazine is obtained by dissolving 15 g. of the compound prepared as described under (c) in 500 ml. of toluene. 5 g. of palladium deposited on asbestos are added thereto. Hydrogen is passed into the solution under a positive pressure of 15 mm. mercury. Progress of the hydrogenating debenzylation is ascertained by thin-layer chromatography. Introduction of hydrogen is discontinued after 20 hours. The catalyst is filtered off. The toluene is distilled off and the residue is triturated with petroleum ether. The precipitated crystals are filtered off by suction. The filter residue is dissolved in warm acetone and is precipitated by the addition of petroleum ether. After filtering off by suction the precipitate and drying it, white crystals of the melting point 108°–112° C. are obtained.

EXAMPLE 36

1-(3,4-Dihydroxy benzyl)-2-phenyl-4-diethylaminoethyl piperazine

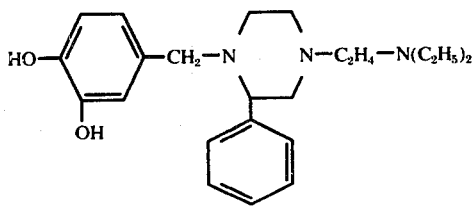

The compound is prepared in an analogous manner as described in Example 35 by using as starting material 1-(3,4-dibenzyloxybenzyl)-2-phenyl-3-keto piperazine. Light yellow, very viscous oil. Boiling point: 245° C./0.001 mm.

EXAMPLE 37

4-Diethylaminoethyl-3-phenyl-1-(3,4-dibenzyloxy benzyl) piperazine hydrochloride.

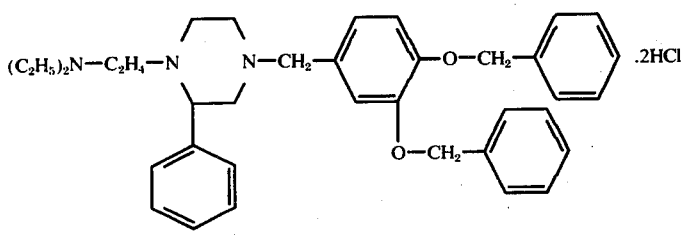

30 g. of 3,4-dibenzyloxy benzylchloride, 23 g. of 1-diethylamino ethyl-2-phenyl piperazine, 20 ml. of triethylamine, and 200 ml. of methylethylketone are boiled under reflux for 12 hours. The precipitated triethylamine hydrochloride is filtered off by suction. The solvent is distilled off and the residue is dissolved in benzene. The benzene solution is extracted with dilute hydrochloric acid (1 : 8). The hydrochloric acid extract is rendered alkaline by the addition of ammonia and is extracted with benzene. The benzene is removed from the benzene extract by distillation. Water-free alcoholic hydrochloric acid is added to the residue, and the hydrochloride of the resulting base is precipitated by the addition of a mixture of petroleum ether and acetone (1 : 1). The hydrochloride is redissolved in alcohol and is again precipitated by the addition of petroleum ether and acetone. Melting point of the hydrochloride: It starts to sublimate at 203° C. and melts at 235°–239° C. with decomposition. White crystals.

EXAMPLE 38

1-(p-Chloro benzyl)-2-phenyl-4-morpholino ethyl-3-keto piperazine

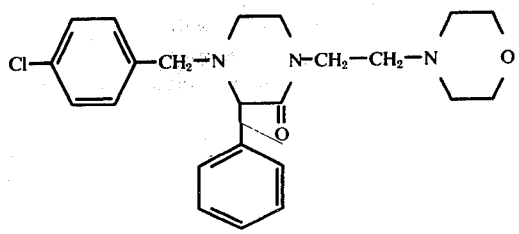

45 g. of 1-(4-chloro benzyl)-2-phenyl-3-keto piperazine,
56 g. of morpholino ethylchloride,
50 g. of potassium carbonate, and
500 ml. of toluene
are boiled under reflux for 20 hours. Water is added to the reaction mixture and undissolved matter is filtered off therefrom. The clear toluene solution is extracted with 250 ml. of N hydrochloric acid. The extract is rendered strongly alkaline by the addition of ammonia and the precipitated base is extracted with benzene. After drying the benzene extract, the solvent is distilled off and the residue is recrystallized from isopropanol, yielding a first crystal fraction. The mother lye is concentrated by evaporation to a small volume and is cooled. Precipitated crystals are filtered off by suction. They represent the second crystal fraction. Since both fractions still contain unreacted starting material, they are triturated with 60 ml. of N acetic and undissolved matter is filtered off. The clear acetic acid solution is rendered strongly alkaline by the addition of ammonia and is extracted with benzene. The benzene is distilled off after drying the extract. The remaining residue is recrystallized from isopropanol. Melting point: 117°–119° C. Yield: 10 g.

EXAMPLE 39

1-(2-Chloro benzyl)-2-phenyl-4-morpholino ethyl-3-keto piperazine

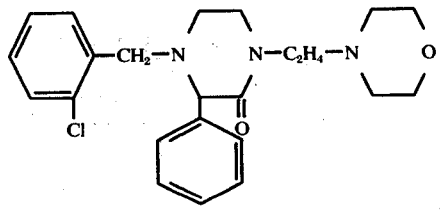

45 g. of 1-(2-chloro benzyl)-2-phenyl-3-keto piperazine obtained as described in Example 46 (a),
56 g. of morpholino ethyl chloride,
50 g. of potassium carbonate, and
500 ml. of toluene are boiled under reflux for 20 hours. The reaction mixture is poured into water. Undissolved matter is separated. The toluene solution is extracted with 250 ml. of N hydrochloric acid. The hydrochloric acid extract is rendered strongly alkaline by the addition of ammonia and the precipitated base is extracted with benzene. After drying, the solvent is distilled off from the extract. The residue is dissolved in 100 ml. of N acetic acid. The crystals formed after allowing the solution to stand for a short period of time, are separated. The acetic acid filtrate is rendered strongly alkaline by the addition of ammonia and the precipitated base is extracted with benzene. After drying the benzene extract and distilling off the solvent, the residue is recrystallized from ispropanol. Melting point: 104°–106° C. Yield: 8.5 g.

EXAMPLE 40

1-(p-Chloro benzyl)-2-phenyl-4-dimethylamino propyl piperazine

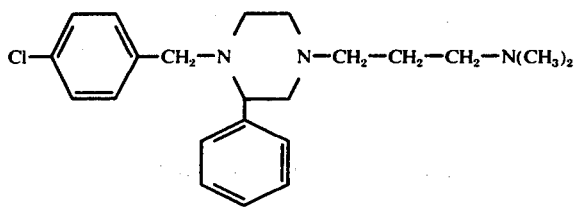

28.6 g. of 1-(p-chloro benzyl)-2-phenyl piperazine,
15.0 g. of dimethylaminopropylchloride,
50 ml. of triethylamine, and
100 ml. of methyl ethyl ketone are boiled under reflux for 20 hours. After cooling, the precipitated triethylamine hydrochloride is filtered off by suction. The solvent is distilled off. The residue is dissolved in 100 cc. of N hydrochloric acid. The hydrochloric acid extract is twice washed with benzene and is then rendered alkaline by the addition of ammonia. The oily base is separated in a separating funnel and is dissolved in 100 ml. of isopropanol. Solid potassium hydroxide is added to the isopropanol solution in order to remove the water present therein. The isopropanol solution is then filtered through a layer of potassium carbonate. After distilling off the solvent, a yellow viscous oil is obtained. The oil is dissolved in 1.5 liters of petroleum ether. Small amounts of impurities are filtered off and the petroleum ether is distilled off. The crude base is dissolved in benzene and is extracted with 25% acetic acid. The base is set free from said extract by the addition of ammonia. The base is again dissolved in benzene and dried by means of potassium carbonate. The solvent is distilled off and the residue is distilled in a vacuum. Boiling point: 180°–184° C./0.08 mm. Yield: 14 g.

EXAMPLE 41

1-(3,4-Dibenzyloxy benzyl)-2-phenyl-4-diethylamino ethyl piperazine fumarate

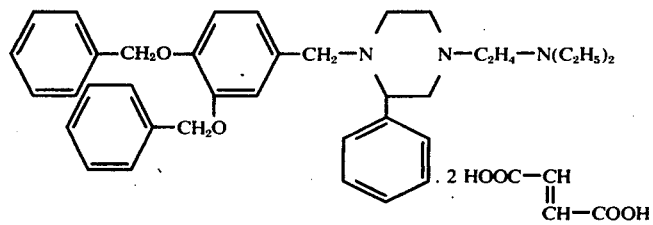

a. 23.2 g. of 2-phenyl-3-keto piperazine,
50.0 g. of 3,4-dibenzyloxy benzylchloride,
30 ml. of triethylamine, and
300 ml. of methyl ethyl ketone are boiled under reflux for 3 hours. After cooling, precipitated triethylamine hydrochloride is filtered off by suction. The solvent is then distilled off. The residue is dissolved in 50 ml. of acetone. The acetone solution is poured into 500 ml. of water. The precipitated crystallized product is filtered off and is twice recrystallized from isopropanol. Melting point: 108°–110° C. Yield 46 g.

b. 44 g. of the compound as described hereinabove under (a) are suspended into
250 ml. of dioxane.

The suspension is added drop by drop to a suspension of
7 g. of lithium aluminum hydride in
500 ml. of ether.

Thereafter the reaction mixture is boiled under reflux for one hour. After decomposing the lithium aluminum hydride complex compound, the ethereal solution is separated, the ether is distilled off, and the residue is recrystallized from isopropanol. Melting point: 54°–55° C. Yield: 25 g.

c. 25 g. of the compound obtained as described hereinabove under (b),
9 g. of diethylamino ethylchloride,
15 ml. of triethylamine, and
150 ml. of methyl ethyl ketone are boiled under reflux for 10 hours. After cooling, the precipitated triethylamine hydrochloride is filtered off by suction. The filtrate is evaporated by distillation to dryness and the residue is dissolved in benzene. The benzene solution is washed with 20% sodium hydroxide solution. The washed benzene layer is separated and extracted with 150 ml. of N hydrochloric acid. The base is set free from said hydrochloric acid extract by the addition of ammonia. It is extracted therefrom with benzene. The benzene solution is dried and the solvent is distilled off. The residue is dissolved in 100 ml. of acetone. 5 g. of fumaric acid are added to said solution which is heated to boiling on the water bath. Small amounts of insoluble matter are filtered off and the solution is cooled. The precipitated fumarate is recrys-

EXAMPLE 42

1-(o-benzyloxy-benzyl)-2-phenyl-4-diethylamino ethyl piperazine

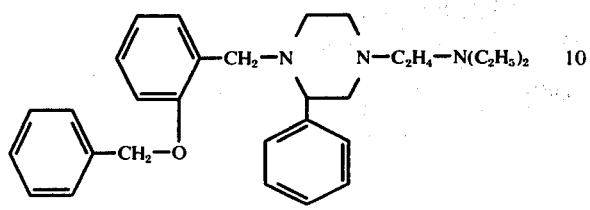

a. 38 g. of 2-phenyl-3-keto piperazine,
52 g. of o-benzyloxy benzylchloride,
50 ml. of triethylamine, and
400 ml. of methyl ethyl ketone are boiled under reflux for four hours. After cooling, the precipitated triethylamine hydrochloride is filtered off by suction. The methyl ethyl ketone is distilled off. The residue is dissolved in isopropanol and water is added thereto, while heating, until crystallization sets in. Melting point: 159°–160° C. Yield: 50 g.

b. 39 g. of the compound prepared as described hereinabove under (a) are dissolved in
100 ml. of anhydrous dioxane.

The solution is added drop by drop to a suspension of
10 g. of lithium aluminum hydride in 900 ml. of absolute ether. Thereafter the mixture is boiled under reflux for one and a half hours. The resulting lithium aluminum hydride complex compound is decomposed by a treatment with 10 ml. of 15% sodium hydroxide solution followed by a treatment with 10 ml. of water, 30 ml. of 15% sodium hydroxide solution, and finally 20 ml. of water. The solution is filtered. The solvent is distilled off. The residue is dissolved in benzene and the benzene solution is extracted with 300 ml. of N/2 hydrochloric acid. The hydrochloric acid extract is rendered strongly alkaline by the addition of ammonia. The precipitated base is extracted with benzene. The benzene solution is dried and the benzene is distilled off. The remaining base is distilled in a vacuum. Boiling point: 205° C./0.03 mm. The base is then recrystallized twice from n-heptane. Melting point: 82°–85° C. Yield: 35 g.

c. 30 g. of the compound prepared as described hereinabove under (b),
12.5 g. of diethylamino ethylchloride,
30 ml. of triethylamine, and
150 ml. of methyl ethyl ketone are boiled under reflux for 12 hours. After cooling, the precipitated triethylamine hydrochloride is filtered off by suction. The solvent is distilled off from the filtrate. The residue is dissolved in benzene. The benzene solution is extracted with 300 ml. of N hydrochloric acid. The base is precipitated from the hydrochloric acid extract by the addition of ammonia. The precipitated base is then extracted with benzene. The benzene solution is dried by means of potassium carbonate and the solvent is distilled off. The residue is distilled in a vacuum. Boiling point: 230°–235° C./0.03 mm. Yield: 25 g.

EXAMPLE 43

1-(p-Methoxy benzyl)-2-phenyl-4-diethylamino propyl piperazine

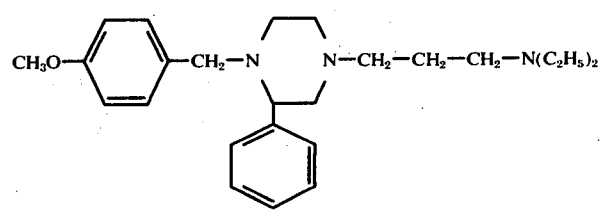

28 g. of 1-(p-methoxy benzyl)-2-phenyl piperazine obtained as described hereinabove in Example 3 (b),
20 g. of diethylamino propylchloride,
50 ml. of triethylamine, and
200 ml. of methyl ethyl ketone are boiled under reflux for 12 hours. Precipitated triethylamine hydrochloride is filtered off. The solvent is removed by distillation. The residue is dissolved in benzene. The benzene solution is extracted with an acetic acid-water mixture 1 : 7). The acetic acid solution is separated from the benzene solution and is rendered alkaline by the addition of ammonia. The precipitated oily base is extracted in benzene, dried by means of potassium carbonate, and the benzene is distilled off. The remaining base is distilled in a vacuum. Boiling point: 200° C./0.01 mm.

The crude base is dissolved in 100 ml. of absolute ethanol and the solution is acidified by the addition of absolute alcoholic hydrochloric acid to a pH of 1.0. The precipitated hydrochloride is filtered off by suction and dried. The salt starts to sublimate at 200° C. and melts at 228°–231° C. with decomposition. The hydrochloride is dissolved in water. The base is set free by the addition of ammonia and is extracted with benzene. The benzene is distilled off from the benzene solution. The remaining base is again distilled in a vacuum. Boiling point: 210° C./0.02 mm. Colorless oil. Yield: 21 g.

EXAMPLE 44

1-(3-Chloro benzyl)-2-phenyl-4-diethylamino ethyl piperazine

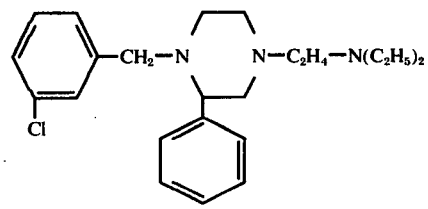

a. 17.5 g. of 1-(3-chloro benzyl)-2-phenyl-3-keto piperazine obtained as described in Example 44 (a) of Application Ser. No. 333,497 are suspended in 50 ml. of absolute dioxane. The suspension is added drop by drop, while stirring, to a suspension of
- 4.5 g. of lithium aluminum hydride in
- 400 ml. of absolute ether.

Thereafter, the reaction mixture is boiled under reflux for one and a half hours. The resulting complex compound is decomposed by a treatment first with
- 4.5 ml. of 15% sodium hydroxide followed by a treatment with 4.5 ml. of water,
- 14.5 ml. of 15% sodium hydroxide solution, and finally 9.0 ml. of water.

The hydroxide precipitate is filtered off and the solvent is distilled off from the filtrate. The residue is dissolved in 20 ml. of N acetic acid. After allowing the solution to stand for 24 hours, the solid precipitate is filtered off. The filtrate is rendered alkaline by the addition of ammonia and the precipitated base is extracted with benzene. After drying the benzene solution, the solvent is distilled off. The residue is dissolved in 30 ml. of absolute ethanol and is adjusted to a pH of 1.0 by the addition of absolute alcoholic hydrochloric acid. The precipitated hydrochloride is filtered off by suction and dried. Melting point: 239°–242° C. The hydrochloride is dissolved in water. The base is set free by the addition of ammonia and is extracted with benzene. After drying the benzene solution and distilling off the benzene, the oily residue is distilled in a vacuum. Boiling point: 145° C./0.05 mm. Colorless oil.

b. 10 g. of the base obtained as described hereinabove under (a),
- 150 ml. of acetone,
- 9.0 g. of diethylamino ethylchloride, and
- 10 ml. of triethylamine are boiled under reflux for 14 hours. The reaction mixture is cooled and the precipitated triethylamine hydrochloride is filtered off by suction. The filtrate is evaporated to dryness. The residue is dissolved in benzene. The benzene solution is extracted with 100 ml. of N hydrochloric acid. The hydrochloric acid extract is rendered alkaline. The precipitated base is extracted with benzene. The benzene solution is then dried by means of potassium carbonate and the benzene is distilled off. The remaining residue is distilled in a vacuum. Boiling point: 170° C./0.07 mm. Yellowish, mobile oil. Yield: 12 g.

EXAMPLE 45

1-(2-Chloro benzyl)-2-phenyl-4-diethylamino ethyl piperazine

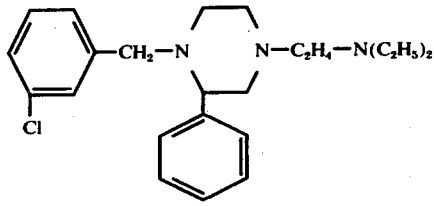

a. 51 g. of 1-(2-chloro benzyl)-2-phenyl-3-keto piperazine prepared as described in Example 46 (a) of Application Serial No. 333,497 are suspended in
- 100 ml. of dioxane.

The suspension is added to a suspension of
- 11 g. of lithium aluminum hydride in
- 700 ml. of absolute ether and
- 50 ml. of dioxane, while stirring. Thereafter, the reaction mixture is boiled under reflux for one and a half hours. The resulting complex compound is decomposed first by a treatment with
- 11 ml. of 15% sodium hydroxide solution followed by a treatment with
- 11 ml. of water,
- 33 ml. of 15% sodium hydroxide solution, and finally with
- 22 ml. of water.

After filtering off by suction the hydroxide precipitate, the solvent is distilled off from the filtrate. The residue is dissolved in 100 ml. of absolute ethanol and 35 ml. of alcoholic hydrochloric acid (about 8 N) are added thereto. The precipitated hydrochloride is filtered off by suction, washed, and dried. Melting point: 276°–277° C. The hydrochloride is dissolved in water. The base is set free therefrom by the addition of ammonia and is extracted with benzene. The benzene solution is dried and the solvent is distilled off. The remaining base is distilled in a vacuum. Boiling point: 136° C./0.08 mm. Yield: 38 g.

b. 10 g. of the base obtained as described hereinabove under (a),
- 150 ml. of acetone,
- 9 g. of diethylamino ethylchloride, and
- 10 ml. of triethylamine are boiled under reflux for 14 hours. The reaction mixture is cooled and the precipitated triethylamine hydrochloride is filtered off by suction. The filtrate is then evaporated to dryness. The residue is dissolved in water and is extracted with benzene. The benzene solution is separated from the aqueous phase and is extracted with 50 ml. of N hydrochloric acid. The hydrochloric acid extract is rendered alkaline by the addition of ammonia and the base set free thereby is extracted with benzene. The benzene solution is dried by means of potassium carbonate and the solvent is distilled off. The residue is distilled in a vacuum. Boiling point: 160° C./0.05 mm. Yield: 11.5 g.

EXAMPLE 46

1-(3-Trifluoromethyl benzyl)-2-phenyl-4-diethylamino ethyl piperazine

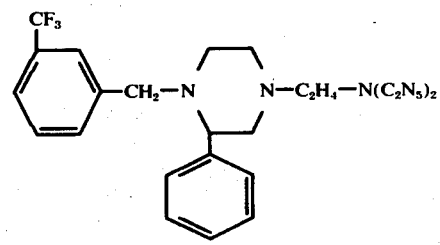

a. 60 g. of 1-(3-trifluoromethyl benzyl)-2-phenyl-3-keto piperazine prepared as described in Example 51 (a) of Application Serial No. 333,497 are dissolved in 120 ml. of dioxane.

The solution is added drop by drop to a suspension of
- 14 g. of lithium aluminum hydride in
- 700 ml. of absolute ether and
- 50 ml. of dioxane, while stirring. Thereafter, the reaction mixture is boiled under reflux for two hours. The resulting complex compound is decomposed first by a treatment with 14 ml. of 15% sodium hydroxide solution followed by a treatment with
14 ml. of water,
42 ml. of 15% sodium hydroxide solution, and finally
28 ml. of water.

The hydroxide precipitate is filtered off and the solvent is distilled off from the filtrate. The residue is dissolved in 200 ml. of absolute ethanol and 35 ml. of an absolute alcoholic solution of hydrochloric acid (8 N) added thereto. The precipitated hydrochloride is filtered off by suction. It is washed with a mixture of acetic acid ethyl ester and alcohol (1 : 1) and is dried. The resulting hydrochloride is dissolved in a small amount of water. The base is set free from said solution by the addition of ammonia and is extracted with benzene. The benzene solution is dried and the solvent is distilled off. The remaining base is distilled in a vacuum. Boiling point: 120° C./0.05 mm. Yield: 40 g.

b. 10 g. of the base obtained as described hereinabove under (a),
150 ml. of acetone,
9 g. of diethylamino ethylchloride, and
10 ml. of triethylamine are boiled under reflux for 14 hours. After cooling, the precipitated triethylamine hydrochloride is filtered off by suction. The solvent is distilled off from the filtrate. The residue is dissolved in benzene. The benzene solution is washed once with water and is then extracted with 50 ml. of N hydrochloric acid. The hydrochloric acid extract is rendered alkaline by the addition of ammonia. The base set free thereby which forms the upper layer is extracted with benzene. The benzene solution is dried and the solvent is distilled off. The remaining base is distilled in a vacuum. Boiling point: 147° C./0.05 mm. Yellowish, mobile oil. Yield: 12.5 g.

EXAMPLE 47

1-(p-Chloro benzyl)-2-phenyl-4-piperazino ethyl piperazine

Cl—⟨C6H4⟩—CH2—N(—C6H5)—N—CH2—CH2—N⟨NH⟩

5 g. of 1-(p-chloro benzyl)-2-phenyl-4-[(3-keto)-piperazino ethyl] piperazine obtained as described hereinabove in Example 23 are dissolved in
100 ml. of absolute dioxane.

The solution is added drop by drop to a suspension of 5 g. of lithium aluminum hydride in 500 ml. of absolute ether. After addition is completed, the reaction mixture is boiled under reflux for two hours. The resulting complex compound is then decomposed first by the addition of
5 ml. of 15% sodium hydroxide solution followed by the addition of
5 ml. of water,
5 ml. of 15% sodium hydroxide solution, and finally
10 ml. of water.

The inorganic hydroxides are filtered off from the reaction mixture and the solvent is distilled off. The residue is dissolved in benzene. The benzene solution is extracted with dilute acetic acid (1 : 10). Ammonia is added to the acetic acid solution. The precipitated base is extracted with benzene. The benzene solution is dried and the benzene is distilled off. The remaining base is distilled in a vacuum. Boiling point: 190° C./0.05 mm. Very viscous yellow oil. Yield: 3 g.

EXAMPLE 48

1-(p-Methoxy benzyl)-2-phenyl-4-piperidino ethyl piperazine

CH3O—⟨C6H4⟩—CH2—N(—C6H5)—N—CH2—CH2—N⟨H⟩

13 g. of 1-(p-methoxy benzyl)-2-phenyl piperazine obtained as described hereinabove in Example 4 (b),
10 g. of piperidino ethylchloride,
40 cc. of triethylamine, and
100 cc. of methyl ethyl ketone are boiled under reflux for 18 hours. Without separating the precipitated triethylamine hydrochloride the solvent is distilled off. The residue is dissolved in benzene and water. The aqueous phase is separated and the benzene solution is extracted with dilute acetic acid (1 : 6). The acetic acid solution is then precipitated by the addition of ammonia. The precipitated base is extracted with benzene, dried by means of potassium carbonate, and the benzene is distilled off. The base is distilled in a vacuum. Boiling point: 210° C./0.001 mm. Light yellow, viscous oil. Yield: 15 g.

EXAMPLE 49

4-Diethylamino ethyl-3-phenyl-(3,4,5-trimethoxy benzyl) piperazine $(C_2H_5)_2N$—$C_2H_4$—N—N—CH2—⟨C6H2(OCH3)3⟩

20 g. of 1-diethylamino ethyl-2-phenyl piperazine prepared as described hereinabove in Example 8 (b),
17 g. of 3,4,5-trimethoxy benzylchloride,
250 ml. of acetone, and
20 ml. of triethylamine are boiled under reflux for 8 hours. After cooling, the precipitated triethylamine hydrochloride is filtered off by suction. The acetone is distilled off in a vacuum. The residue is dissolved in benzene, and the benzene solution is extracted with 50 ml. of N hydrochloric acid. The hydrochloric acid extract is rendered alkaline by the addition of ammonia. The precipitated base is extracted with benzene. After drying by means of potassium carbonate, the solvent is distilled off. The remaining base is distilled in a vacuum. Boiling point: 210° C./0.05 mm. Yellowish, viscous oil. Yield: 19 g.

EXAMPLE 50

4-Diethylamino ethyl-3-phenyl-1-(p-chloro phenyl ethyl) piperazine

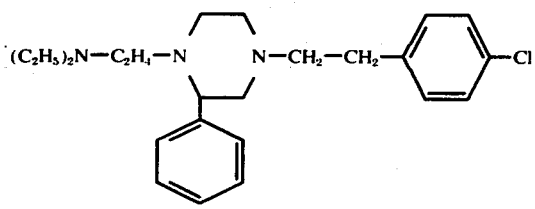

20 g. of 1-diethylamino ethyl-2-phenyl piperazine obtained as described hereinabove in Example 8 (b),
17 g. of p-chloro phenyl ethylchloride,
20 ml. of triethylamine, and
100 ml. of dimethylformamide
are heated on the water bath for 12 hours. The dimethylformamide is then distilled off in a vacuum. The residue is dissolved in acetone. The precipitated triethylamine hydrochloride is filtered off by suction and the acetone is distilled off from the filtrate. The resulting base is dissolved in benzene and extracted with 50 ml. of N hydrochloric acid. The hydrochloric acid extract is precipitated by the addition of ammonia. The precipitated base is extracted with benzene. The benzene solution is dried by means of potassium carbonate and the benzene is distilled off therefrom. The remaining base is distilled in a vacuum. Boiling point: 190° C./0.02 mm. Yield: 13 g.

EXAMPLE 51

4-Diethylamino ethyl-3-phenyl-1-(o-benzyloxy benzyl) piperazine

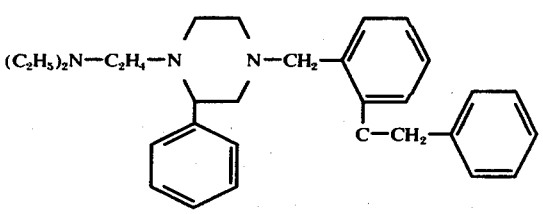

27 g. of 1-diethylamino ethyl-2-phenyl piperazine prepared as described hereinabove in Example 8 (b),
27 g. of 2-benzyloxy benzyl chloride,
25 ml. of triethylamine, and
250 ml. of acetone
are boiled under reflux for 4 hours. The precipitated triethylamine hydrochloride is filtered off by suction. The acetone is removed by distillation. The residue is dissolved in benzene and water. The benzene solution is separated from the aqueous phase and is extracted with 100 ml. of 0.5 N hydrochloric acid. The hydrochloric acid extract is rendered alkaline by the addition of ammonia and the precipitated base is extracted with benzene. After drying the benzene extract, the solvent is distilled off. Boiling point: 232° C./0.03 mm. Yellowish oil. Yield: 26 g.

EXAMPLE 52

4-Diethylamino ethyl-3-phenyl-1-(p-benzyloxy benzyl) piperazine

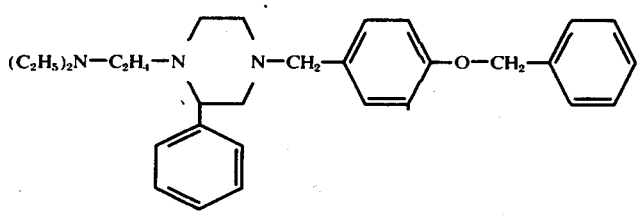

30 g. of 1-diethylamino ethyl-2-phenyl piperazine obtained as described hereinabove in Example 8 (b),
100 ml. of methyl ethyl ketone,
50 ml. of triethylamine, and
24 g. of p-benzyloxy benzylchloride
are boiled under reflux for 12 hours. After cooling, the precipitated triethylamine hydrochloride is filtered off by suction. The methyl ethyl ketone is distilled off from the filtrate. The residue is dissolved in benzene and water. The benzene solution is separated from the aqueous phase and is extracted with 250 ml. of 0.1 N hydrochloric acid. The hydrochloric acid extract is rendered alkaline by the addition of ammonia. The precipitated base is extracted with benzene. The benzene solution is dried and the solvent is distilled off. Boiling point of the remaining base: 245° C./0.005 mm. Yellow, very viscous oil. The base is dissolved in a small amount of ethanol and its hydrochloride is precipitated from the solution by the addition of absolute alcoholic hydrochloric acid. The hydrochloride is filtered off by suction and is dried. The hydrochloride is dissolved in water. The base is set free by the addition of ammonia, extracted with benzene, dried, and the solvent is distilled off. The residue is recrystallized from petroleum ether. Melting point: 58° C. Yield: 33 g.

EXAMPLE 53

4-Diethylamino ethyl-3-phenyl-1-(p-hydroxy benzyl) piperazine

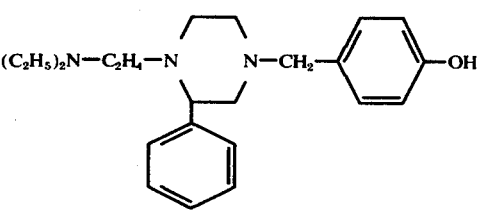

25 g. of 1-diethylamino ethyl-3-phenyl-4-(p-benzyloxy benzyl) piperazine obtained as described hereinabove in Example 52 are dissolved in 500 ml. of toluene. 4 g. of palladium asbestos are added thereto and hydrogen is introduced into the solution at room temperature under a positive pressure of 50 mm. Hg. A white, crystalline compound starts to precipitate on the catalyst after 15 hours. Introduction of hydrogen is discontinued. The catalyst is filtered off by suction and is washed with 500 ml. of 60° C. toluene. The toluene is distilled off and the remaining residue is recrystallized first from n-heptane and subsequently from isopropanol. Melting point: 144° C. Yield: 11 g.

EXAMPLE 54

4-Diethylamino ethyl-3-phenyl-1-benzyl piperazine

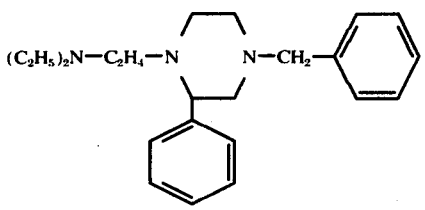

15 g. of 1-diethylamino ethyl-2-phenyl piperazine obtained as described hereinabove in Example 8 (b),
8 g. of benzylchloride,
150 ml. of methyl ethyl ketone, and
20 ml. of triethylamine
are boiled under reflux for 8 hours. After cooling, the precipitated triethylamine hydrochloride is filtered off by suction. The acetone is distilled off and the residue is dissolved in benzene. The benzene solution is extracted with 100 ml. of N-hydrochloric acid. The hydrochloric acid extract is rendered alkaline by the addition of ammonia. The precipitated base is extracted with benzene. The benzene solution is dried and the solvent is distilled off therefrom. The residue is distilled in a vacuum. Boiling point: 160° C./0.01 mm. Yellowish oil. Yield: 10 g.

EXAMPLE 55

4-Diethylamino ethyl-3-phenyl-1-(3,4-dibenzyloxy benzyl) piperazine hydrochloride

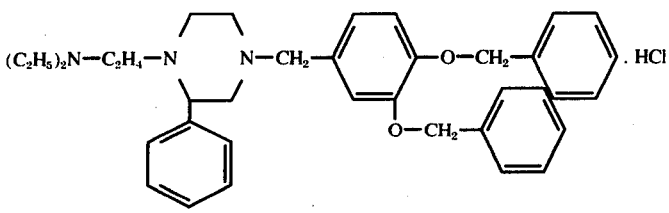

23 g. of 1-diethylamino ethyl-2-phenyl piperazine obtained as described hereinabove in Example 8 (b),
. 30 g. of 3,4-dibenzyloxy benzylchloride,
20 ml. of triethylamine, and
200 ml. of methyl ethyl ketone
are boiled for 12 hours under reflux. The precipitated triethylamine hydrochloride is filtered off by suction. The solvent is distilled off. The residue is dissolved in benzene. The benzene solution is extracted with 100 ml. of N hydrochloric acid. The hydrochloric acid extract is precipitated by the addition of ammonia. The precipitated base is dissolved in benzene, the benzene solution is dried and the solvent is distilled off. Absolute alcoholic hydrochloric acid is added to the residue in an amount to yield a pH of 1.0 and a mixture of petroleum ether and acetone (1:1) is slowly added thereto. The hydrochloride precipitates and is filtered off by suction. It is dissolved in alcohol and is again precipitated by careful addition of a mixture of petroleum ether and acetone (1:1).

The compound obtained after filtering and drying starts to sublimate at 203° C. and has a melting point of 235°–239° C. with decomposition. Yield: 39 g.

EXAMPLE 56

4-Diethylamino ethyl-3-phenyl-1-(p-methoxy benzyl) piperazine

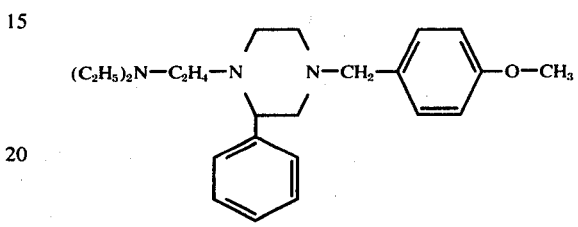

64 g. of 1-diethylamino ethyl-2-phenyl piperazine obtained as described hereinabove in Example 8 (b),
39 g. of p-methoxy benzylchloride,
75 g. of triethylamine, and
500 ml. of acetone
are boiled under reflux for 7 hours. After cooling, the precipitated triethylamine hydrochloride is filtered off by suction. The filtrate is evaporated to dryness. The residue is dissolved in benzene and is extracted with 200 ml. of N hydrochloric acid. Ammonia is added to the hydrochloric acid extract and the precipitated base is extracted with benzene. The benzene solution is dried by means of potassium carbonate and the solvent is distilled off. The residue is distilled in a vacuum. Boiling point: 180°–182° C./0.005 mm. Yellowish oil. Yield: 24 g.

The new 1,4-substituted phenyl piperazine compounds to the present invention and their pharmaceutically acceptable acid addition salts can be administered orally, parenterally, or rectally. Compositions containing said compounds as used in therapy, comprise, for instance, tablets, pills, dragees, lozenges, and the like shaped preparations to be administered orally. Said compounds may also be administered in powder form, preferably enclosed in gelatin or the like capsules. Oral administration in liquid form, such as in the form of solutions, emulsions, suspensions, sirups, and the like is also possible. Such solid or liquid preparations are produced in a manner known to the art of compounding and processing pharmaceutical compositions whereby the conventional diluting, binding, and/or expanding agents, lubricants, and/or other excipients, such as lactose, cane sugar, dextrins, starch, talc, kaolin, magnesium hydroxide, magnesium carbonate, pectin, gelatin, agar, bentonite, stearic acid, magnesium stearate, and others may be employed.

The following examples serve to illustrate the preparation of pharmaceutical compositions as they are used in therapy without, however, limiting the same thereto.

EXAMPLE 57

Tablets:

20 g. of the dihydrochloride of 1-(4'-chloro benzyl)-2-phenyl-4-diethylamino ethyl piperazine, 128 g. of lactose, and 2 g. of magnesium stearate are intimately mixed with each other and are compressed without preceding granulation to tablets weighing 150 mg. Each tablet contains 20 mg. of the anticoagulant agent according to the present invention.

EXAMPLE 58

The mixture of ingredients as given in Example 57 is compressed to biconvex dragee cores of 150 mg. each. These cores are repeatedly sugar-coated by rotating in a coating pan with sugar sirup. Each dragee contains 20 mg.

EXAMPLE 59

Capsules:

500 g. of 1-(3',4'-dichloro benzyl)-2-phenyl-4-diethylamino ethyl piperazine dihydrochloride are intimately mixed with 200 g. of starch and the mixture is sieved. Portions of 700 mg. each of said mixture are filled in gelatin capsules. Each capsule contains 500 mg. of the anticoagulant agent.

EXAMPLE 60

Suppositories:

400 g. of the molten suppository base Adeps solidus and 10 g. of the succinate of 1-(4'-chloro benzyl)-2-phenyl-4-piperidino ethyl piperazine are thoroughly triturated while maintaining in the molten state. The molten mixture is cast into suppository molds, each of which contains 2.05 g. of the mixture. The molds are then cooled to cause solidification. Each suppository contains 50 mg. of the anticoagulant agent.

EXAMPLE 61

25 mg. of 1-(4'-chloro benzyl)-2-phenyl-4-diethylamino ethyl piperazine dihydrochloride are dissolved in 2.2 cc. of bidistilled water. This solution is filled in ampoules which are sterilized in an autoclave at 120° C.

Ampoules containing 5 mg. to 250 mg. of base may be prepared as follows: The base is dissolved in water by the addition of a stoichiometrically equivalent amount of the desired acid. As an acid, there may be used e.g. hydrochloric acid, phosphoric acid, nitric acid, sulfuric acid, succinic acid, fumaric acid, lactic acid, and the like.

The effect which 1,4-disubstituted phenyl piperazine compounds according to the present invention have on blood coagulation, was determined according to standard test methods in vitro with human blood. The results of such tests are given in the following Table. The test mixture was prepared by adding one part of the aqueous solution of the compound to be tested to 9 parts of plasma. The compound to be tested was used in the form of its hydrochloride. Thus 0.1 millimole (mM) as given in the Table indicates 9 ml. of plasma plus 1 ml. of a millimolar (mM) aqueous solution of the compound to be tested.

The effect of the compounds according to the present invention was determined by measuring the recalcification time as well as the stypven time.

The determination of the recalcification time is based on the fact that free calcium$^{++}$ions are required to cause coagulation. Because the calcium ions are bound in the blood which has been rendered non-coagulable by the addition of citrate or oxalate, excess calcium chloride solution is added in this test and the period of time calculated from the additon of the calcium chloride to the onset of coagulation is measured. This period of time is the recalcification time.

For determining the stypven time, there is added, in addition to the calcium ions, the viper poison stypven to the citrate or oxalate blood. The stypven test is an especially sensitive test for detecting lipides set free from the thrombocytes.

In order to determine the effect of the compounds according to the present invention upon thrombocytes which are principal features with respect to coagulation of blood, the recalcification time and the stypven time were determined in blood rich in thrombocytes as well as in blood poor in thrombocytes.

It is assumed that the formation of blood clots is initiated by thrombocyte aggregation. Therefore, the compounds according to this invention were also tested for their thrombocyte aggregation, inhibiting effect by the method described by Klaus Breddin in "Schweizerische Medizinische Wochenschrift" vol. 20, p. 655 (1965).

The following Table shows those concentrations of the tested compounds, determined by means of their recalcification time and their stypven time, which indicate a pronounced blood coagulation promoting effect as well as a pronounced blood coagulation inhibiting effect. These concentrations are given in millimoles of the respective compound. The concentrations at which inhibition of the thrombocyte aggregation sets in, are also given for some of the compounds. That one and the same compound can have a blood coagulation promoting as well as a blood coagulation inhibiting effect, is due to the fact that it acts upon various coagulation factors at the same time. Thus a compound is able to set free from the thrombocytes coagulation activating material at a low concentration while at a higher concentration certain coagulation factors have an inhibiting effect.

o in said Table indicates that no effect has been found within the tested concentration range.

The recalcification time was determined according to the method of E. DEUTSCH ET AL. in "Thrombosis et Diathesis Haemorrhagica" vol. XXVI, page 145(1971) and the stypven time according to the method of McKENZIE ET AL. in "Amer. Journ. Clin. Path." vol. 55, pages 551-554.

It has also been found that a number of the compounds according to the present invention possess fibrinolytic activity, i.e. they are capable of dissolving thrombi which have been formed.

TABLE

| Example No. | Compound | Molecular weight | Coagulation promoting effect Plasma rich in thrombocytes mM | Coagulation promoting effect Plasma poor in thrombocytes mM | Coagulation inhibiting effect Plasma rich in thrombocytes mM | Coagulation inhibiting effect Plasma poor in thrombocytes mM | Inhibition of thrombocytes aggregation according to Breddin mM |
|---|---|---|---|---|---|---|---|
| 1 | 1-(4-Chloro benzyl)-2-phenyl-4-diethylamino-ethyl-3-keto-piperazine | 399.9 | 1 | 1 | 55 | 5 | 0.1 |
| 2 | 4-Diethylaminoethyl-2-phenyl-1-(4-chloro benzyl) piperazine | 386.0 | 1 | 1 | 5 | 5 | 1 |
| 3 | 1-(3,4-Dichloro benzyl)-2-phenyl-4-diethylaminoethyl-piperazine | 420.4 | 0.1 – 1 | 1 | 2.5 | 2.5 | 0.1 |
| 4 | 1-(p-Methoxyphenyl-ethyl)-2-phenyl-4-Methylamino ethyl piperazine | 395.5 | 1 | 1 | 10 | 5 | 0.1–0.5 |
| 5 | 1-(3-Phenylpropyl)-2-phenyl-4-diethylamino-ethyl piperazine | 379.5 | 0.1 – 1 | 1 | 5 | 2.5 | 0.1–0.5 |
| 5 | 1-(4-Chloro benzyl)-2-phenyl-4-(2-piperidino ethyl) piperazine | 397.9 | 1 | 1 | 5 | 2.5–5 | 0.1 |
| 5 | 1-(p-chloro benzyl)-2-phenyl-4-[(4-methyl)-piperazine ethyl-(1)]piperazine | 413.01 | 0.1 | 0.1 | 2.5 | 2.5 | 0.1 |
| 5 | 1-(p-Chloro benzyl)-2-phenyl-4-pyrrolidino ethyl piperazine | 383.97 | 0.1 | 1 | 5 | 2.5 | 0.5 |
| 6 | 1-(4-Chloro benzyl)-2-phenyl-4-(1,3-bis-(morpholino propyl) piperazine | 499.08 | 1 | 1 | 5 | 2.5 | 0.1–1 |
| 7 | 1-(p-Chloro benzyl)-3-phenyl-4-diethylamino ethyl piperazine | 386.1 | 0.1 | 1 | 5 | 2.5 | 0.01–0.1 |
| 8 | 4-Diethylaminoethyl-3-phenyl-1-(p-ethoxy benzyl)piperazine | 395.6 | 0.1–1 | 1 | 5 | 1–2.5 | 0.01–0.1 |
|  | 4-Diethylaminoethyl-3-phenyl-2-keto-1-(p-chloro benzyl) piperazine | 399.95 | 1 | 1 | 5 | 2.5–5 | 0.1 |
| 14 | 4-Dimethylaminoethyl-2-phenyl-1-(3,4-dichloro benzyl)-piperazine | 392,38 | 0.1 | 1 | 2.5 | 2.5 | 0.1–0.5 |
| 15 | 4-β-Morpholinoethyl-2-phenyl-(3,4-dichloro benzyl)piperazine | 434.42 | 1 | 1 | — | — | 0.1 |
| 16 | 4-Diethylaminopropyl-2-phenyl-1-(3,4-dichloro benzyl) piperazine | 434,462 | 0.1 | 1 | 2.5 | 2.5 | 0.01 |
| 17 | 1-(4-Benzyloxy benzyl)-2-phenyl-4-diethylaminoethyl piperazine | 457,66 | 0.1 | 0.1 | 2.5 | 2.5 |  |
| 18 | 4-Diethylaminoethyl-2-phenyl-1-(3,4,5-trimethoxy benzyl) piperazine | 4.41.596. 1 | — | — | 5 | 0.1 |  |
| 19 | 1-[(p-Methoxy phenyl propyl)]-2-phenyl-4-diethylaminoethyl piperazine | 409,626 | 0.1 | 1 | 5 | 5 | 0.1–0.5 |
| 20 | 4-Diethylaminoethyl-3-phenyl-1-(p-ethoxy benzyl)piperazine | 395,6 | 0.1–1 | 1 | 5 | 1 – 2.5 | 0.1–0.5 |
| 22 | 1-(p-Chloro benzyl-2-phenyl-4-[(4-methyl)piperazino ethyl-(1)]piperazine | 413.01 | 0.1 | 0.1 | 5 | 2.5 |  |
| 23 | 1-(p-Chlorobenzyl)-2-phenyl-4-[3-keto)-piperazinoethyl)-(1)] piperazine | 466.99 | 0.1 | 0.5 | o | o |  |
| 5a | 1-(p-Chloro benzyl)-2-phenyl-4-pyrrolidino ethyl piperazine | 383,97 | 1 | o | 5 | 2.5 |  |
| 34 | 4-Diethylaminoethyl-3-phenyl-1-(o-hydroxy benzyl) piperazine | 367.5 | 1 | 1 | 5 | 5 | — |
| 36 | 4-Diethylaminoethyl-3-phenyl-1-(3,4,5-trimethoxybenzyl) piperazine | 441.5 | 1 | o | o | 2.5 | — |
| 37 | 1-(p-Hydroxy benzyl)-2-phenyl-4-diethylaminoethyl piperazine | 367.5 | 1 | 1 | o | o | — |
|  | 1-(p-Ethoxy benzyl)-2-phenyl-4-pyrrolidinoethyl-3-keto piperazine | 407,53 | 1 | 1 | o | 5 |  |
| 47 | 1-(p-Chloro benzyl)-2-phenyl-4-piperazino ethyl piperazine | 399.0 | 0.1 | 0.1 | 2.5 | 5 |  |
| 48 | 1-(p-Methoxy benzyl)-2-phenyl-4-piperidinoethyl piperazine | 393.55 | 1 | o | 5 | 2.5 |  |
| 49 | 4-Diethylaminoethyl-3-phenyl-1-(3,4,5-trimethoxy)- |  |  |  |  |  |  |

TABLE-continued

| Example No. | Compound | Molecular weight | Coagulation promoting effect Plasma rich in thrombocytes mM | Coagulation promoting effect Plasma poor in thrombocytes mM | Coagulation inhibiting effect Plasma rich in thrombocytes mM | Coagulation inhibiting effect Plasma poor in thrombocytes mM | Inhibition of thrombocytes aggregation according to Breddin mM |
|---|---|---|---|---|---|---|---|
| | benzyl piperazine | 441,5 | 1 | o | o | 2.5 | |
| 50 | 4-Diethylaminoethyl-3-phenyl-1-(p-chloro phenyl)ethyl piperazine | 400.00 | 0.1 | o | 5 | 2.5 | 0.05 |
| 51 | 4-Diethylamino ethyl-3-phenyl-1-(o-benzyloxy benzyl) piperazine | 457.66 | 0.1 | o | 5 | 0.1 | |
| 52 | 4-Diethylaminoethyl-3-phenyl-1-(p-benzyloxy benzyl) piperazine | 457.66 | 0.1 | 1 | 2.5 | 2.5 | 1 |
| 53 | 4-Diethylaminoethyl-3-phenyl-1-(p-hydroxy benzyl)piperazine | 367.5 | 0.1 | o | 10 | 5 | — |
| 54 | 4-Diethylamino ethyl-3-phenyl-1-benzyl piperazine | 351.54 | 0.1 | 0.1 | 0 | o | |
| 55 | 4-Diethylaminoethyl-3-phenyl-1-(3,4-dibenzyloxy benzyl)piperazine . HCl | 563.79 | 1 | 0.1 | 2.5 | o | |
| | 4-Diethylaminoethyl-3-phenyl-2-keto-1-(p-benzyloxy benzyl) piperazine | 471.65 | 1 | 1 | 10 | 2.5 | |
| 40 | 1-(p-Chloro benzyl)-2-phenyl-4-dimethylamino propyl piperazine | 371,94 | 0.01 | 0.1 | 2.5 | 2.5 | |
| 41 | 1-(3,4-Dibenzyloxy benzyl)-2-phenyl-diethylaminoethyl piperazine fumarate | 563.79 | 1 | 1 | 2.5 | 2.5 | |
| 42 | 1-(o-Benzyloxy benzyl)-2-phenyl-4-diethylaminoethyl piperazine | 457.66 | 0.1 | 1 | 5 | 2.5 | |
| 43 | 1-(p-Methoxybenzyl)-2-phenyl-4-diethylamino propyl piperazine | 395,57 | 0.1 | o | 5 | 5 | |

The starting materials are either commercially available or can be synthesized from commercially available compounds by known methods.

For instance, α-chloro phenyl acetic acid ethyl ester used as the one reactant in Example 1 B (a), is prepared from commercially available α-chloro phenyl acetic acid chloride by esterifying with ethanol. Its boiling point is 123°–125° C./8-10 mm.

$N_1$-(diethylamino ethyl) ethylene diamine, the other reactant of Example 1 B (a) is obtained according to the method of H. F. McKay "Canad. J. Chem." vol. 34, pp. 1567-1573 (1956).

1-(β-Chloro ethyl)-4-methyl piperazine used as reactant in Example 6, is prepared by reacting 1(β-hydroxy ethyl)-4-methyl piperazine and thionylchloride.

1,3-Dimorpholino propylchloride (Example 7) is obtained by reacting 1,3-dimorpholino propanol with thionylchloride.

p-Ethoxy benzylchloride (Example 9 c) is produced according to Bergmann and Sulzbacher "J. org. Chem." vol. 16, p. 85 (1951).

3,4,5-Trimethoxy benzylchloride (Example 13) is prepared by reacting 3,4,5-trimethoxy benzyl alcohol with thionylchloride and 3-(4′-Methoxy phenyl) propylchloride (1) by reacting 3-(4′-methoxy phenyl) propanol (1) with thionylchloride.

Acetyl glycolic acid chloride (Example 27 A c) is obtained according to Ghosh "J. Indian Chem. Soc." vol. 24, p. 325 (1947) from acetyl glycolic acid synthesized according to Anschuetz et al. "Ber." vol. 30, p. 467.

1-(3,4-Dibenzyloxy benzyl)-2-phenyl-3-keto piperazine (Example 42) is obtained by reacting 2-phenyl-3-keto piperazine with 3,4-dibenzyloxy benzylchloride. Its melting point is 108°–110° C.

3,4-Dibenzyloxy benzylchloride (Example 43) is synthesized by first producing 3,4-dibenzyloxy benzaldehyde according to the method described by Bergmann et al. "J. org. Chem." vol. 16, p. 85 (1951), reducing said aldehyde with sodium boron hydride to the corresponding alcohol, and chlorinating the resulting alcohol with thionylchloride in chloroform. Melting point of the chloride: 42°–44° C.

o-Benzyloxy benzylchloride (Example 55) is obtained in an analogous manner. Boiling point: 118° C./0.05 mm.

Diethylamino propylchloride (Example 56) is prepared by reacting diethylamino propanol with thionylchloride.

p-Chloro phenyl ethylchloride (Example 63) is synthesized according to Depuy et al. "J. Am. Chem. Soc."vol. 79, pp. 3710-11 soc." (1957) and Baddeley et al. "J. Am. Chem. Soc." 1935, p. 1820.

p-Methoxy benzylchloride (Example 69) is prepared as described in "Org. Synth." vol. 36, p. 50.

The following example describes the preparation of a compound in which $R_4$ and $R_5$ of Formulas VII to XII form an $N_4$-hydroxy lower alkyl piperazine group.

EXAMPLE 62

1-(p-Chloro benzyl)-2-phenyl-4-[β-(4'-hydroxy ethyl piperazino) ethyl ] piperazine

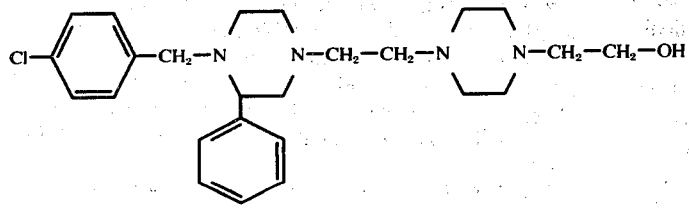

The compound is obtained by reacting 1-(4'-chloro benzyl)-2-phenyl-4-(β-chloro ethyl) piperazine hydrochloride as described hereinabove in Example 21B and C, with $N_1$-(2-hydroxy ethyl) piperazine. The resulting reaction product is a yellow oil of the boiling point: 245° C./0.02 mm.

Analogous compounds in which the phenyl ring of the benzyl or phenyl lower alkyl substituent in 1-position is substituted by other substituents than chloro, as well as compounds of the 3-phenyl piperazine type or the 2- or 3-phenyl-3- or -2-keto piperazine type and which have in 4-position a hydroxy lower alkyl piperazino lower alkyl group can, of course, also be produced in a similar manner.

We claim:

1. A 1,4-disubstituted phenyl piperazine compound of the formula

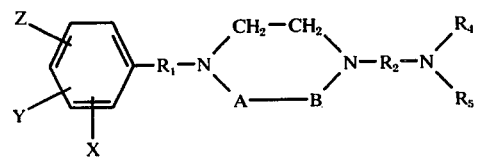

in which

X, Y, and Z are members selected from the group consisting of hydrogen, halogen, trifluoro lower alkyl, hydroxyl, lower alkoxy, and phenyl substituted lower alkoxy;

$R_1$ is lower alkyl with 1 to 3 carbon atoms;

$R_2$ is lower alkyl;

$R_4$ and $R_5$ are members selected from the group consisting of lower alkyl, and, together with the nitrogen to which they are attached, form piperidino or pyrrolidino; and one of the groups A and B is the methylene group of the formula —$CH_2$—, while the other one of the groups A and B is the phenyl substituted methylene group of the formula

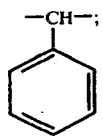

or their pharmaceutically acceptable acid addition salts.

2. A 1,4-disubstituted phenyl piperazine compound of the formula

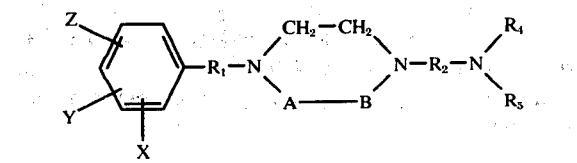

in which

X, Y, and Z are members selected from the group consisting of hydrogen, halogen, trifluoro lower alkyl, hydroxyl, lower alkoxy, and phenyl substituted lower alkoxy;

$R_1$ is lower alkyl with 1 to 3 carbon atoms;

$R_2$, $R_4$, and $R_5$ are lower alkyl; and one of the groups A and B is the methylene group of the formula —$CH_2$—, while the other one of the groups A and B is the phenyl substituted methylene group of the formula

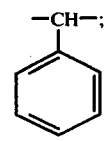

or their pharmaceutically acceptable acid addition salts.

3. The 1,4-disubstituted phenyl piperazine compound of claim 2, said compound being a 1-(phenyl lower alkyl)-3-phenyl-4-(di-lower alkylamino lower alkyl) piperazine or its pharmaceutically acceptable acid addition salts.

4. The 1,4-disubstituted phenyl piperazine compound of claim 2, said compound being a 1-(phenyl lower alkyl)-3-phenyl-4-(di-lower alkylamino lower alkyl) piperazine, the phenyl ring in 1-position being substituted by halogen, or its pharmaceutically acceptable acid addition salts.

5. The 1,4-disubstituted phenyl piperazine compound of claim 2, said compound being a 1-(phenyl lower alkyl)-3-phenyl-4-(di-lower alkylamino lower alkyl) piperazine, the phenyl ring in 1-position being substituted by lower alkoxy, or its pharmaceutically acceptable acid addition salts.

6. The 1,4-disubstituted phenyl piperazine compound of claim 2, said compound being a 1-(phenyl lower alkyl)-2-phenyl-4-(di-lower alkylamino lower alkyl) piperazine or its pharmaceutically acceptable acid addition salts.

7. The 1,4-disubstituted phenyl piperazine compound of claim 2, said compound being a 1-(phenyl lower alkyl)-2-phenyl-4-(di-lower alkylamino lower alkyl) piperazine, the phenyl ring in 1-position being substituted by halogen, or its pharmaceutically acceptable acid addition salts.

8. The 1,4-disubstituted phenyl piperazine compound of claim 2, said compound being a 1-(phenyl lower alkyl)-2-phenyl-4-(di-lower alkylamino lower alkyl) piperazine, the phenyl ring in 1-position being substituted by lower alkoxy, or its pharmaceutically acceptable acid addition salts.

9. The 1,4-disubstituted phenyl piperazine compound of claim 2, said compound being 1-(4'-chloro benzyl)-2-phenyl-4-(diethylamino ethyl) piperazine, or its pharmaceutically acceptable acid addition salts.

10. The 1,4-disubstituted phenyl piperazine compound of claim 2, said compound being 1-(3',4'-dichlorobenzyl)-2-phenyl-4-(diethylamino ethyl) piperazine, or its pharmaceutically acceptable acid addition salts.

11. The 1,4-disubstituted phenyl piperazine compound of claim 1, said compound being 1-(4'-chloro benzyl)-2-phenyl-4-(piperidino ethyl) piperazine, or its pharmaceutically acceptable acid addition salts.

12. The 1,4-disubstituted phenyl piperazine compound of claim 2, said compound being 1-(4'-chloro benzyl)-3-phenyl-4-(diethylamino ethyl) piperazine, or its pharmaceutically acceptable acid addition salts.

13. The 1,4-disubstituted phenyl piperazine compound of claim 2, said compound being 1-[3'-phenyl propyl(1)]-2-phenyl-4-(diethylamino ethyl) piperazine, or its pharmaceutically acceptable acid addition salts.

14. The 1,4-disubstituted phenyl piperazine compound of claim 2, said compound being 1-[(4'-methoxy phenyl)ethyl]-2-phenyl-4-(diethylamino ethyl) piperazine, or its pharmaceutically acceptable acid addition salts.

* * * * *